(12) United States Patent
Kahn et al.

(10) Patent No.: US 7,104,115 B2
(45) Date of Patent: Sep. 12, 2006

(54) FLUID TREATMENT APPARATUS WITH INPUT AND OUTPUT FLUID SENSING

(75) Inventors: Malcolm R. Kahn, Franklin Lakes, NJ (US); Glenn Martin, Farmington Hills, MI (US); Piu Francis Man, Ann Arbor, MI (US)

(73) Assignee: Sensicore, Inc., Ann Arbor, MI (US)

( * ) Notice: Subject to any disclaimer, the term of this patent is extended or adjusted under 35 U.S.C. 154(b) by 0 days.

(21) Appl. No.: 10/840,649

(22) Filed: May 7, 2004

(65) Prior Publication Data

US 2005/0247113 A1    Nov. 10, 2005

(51) Int. Cl.
*G01N 11/00* (2006.01)
(52) U.S. Cl. ..................................... 73/53.01
(58) Field of Classification Search ............. 73/53.01, 73/54.12
See application file for complete search history.

(56) References Cited

U.S. PATENT DOCUMENTS

| | | |
|---|---|---|
| 4,649,515 A | 3/1987 | Thompson et al. |
| 4,743,954 A | 5/1988 | Brown |
| 4,766,550 A | 8/1988 | Byers et al. |
| 4,830,757 A | 5/1989 | Lynch et al. |
| 4,833,622 A | 5/1989 | Barto et al. |
| 4,849,098 A | 7/1989 | Wilcock et al. |
| 4,886,590 A | 12/1989 | Tittle |
| 4,943,161 A | 7/1990 | Michaelis et al. |
| 4,943,929 A | 7/1990 | Simonoff |
| 4,967,337 A | 10/1990 | English et al. |
| 5,102,526 A | 4/1992 | Brown et al. |
| 5,120,421 A | 6/1992 | Glass et al. |
| 5,203,984 A | 4/1993 | Sakai et al. |
| 5,239,483 A | 8/1993 | Weir |
| 5,394,543 A | 2/1995 | Hill et al. |
| 5,417,835 A | 5/1995 | Brown et al. |
| 5,492,632 A | 2/1996 | Reber |
| 5,494,573 A | 2/1996 | Schoenmeyr et al. |
| 5,504,692 A | 4/1996 | Cardner |
| 5,525,297 A | 6/1996 | Dinger et al. |
| 5,607,566 A | 3/1997 | Brown et al. |
| 5,608,171 A | 3/1997 | Hunter et al. |
| 5,631,744 A | 5/1997 | Takeuchi et al. |
| 5,674,397 A * | 10/1997 | Pawlak et al. .............. 210/436 |
| 5,696,696 A | 12/1997 | Gunther et al. |
| 5,724,254 A | 3/1998 | Millett et al. |

(Continued)

FOREIGN PATENT DOCUMENTS

EP    1197753 A2    4/2002

(Continued)

OTHER PUBLICATIONS

M. Kahn et al., Copending U.S. Appl. No. 10/840,628, Monitoring Systems and Methods for Fluid Testing, filed May 7, 2004 (unpublished).

(Continued)

*Primary Examiner*—Hezron Williams
*Assistant Examiner*—Rodney Frank
(74) *Attorney, Agent, or Firm*—Jones Day

(57) ABSTRACT

Various sensor unit configurations are disclosed within the context of a fluid quality monitoring system. The distribution of sensor units can be accomplished using existing product distribution channels to sell, distribute and install sensor units so that a fluid distribution monitoring system can be established at relatively low cost, on a wider basis, and by locating sensor units at the most desirable location from problem detection standpoint, the location of the end user.

55 Claims, 7 Drawing Sheets

U.S. PATENT DOCUMENTS

| | | | |
|---|---|---|---|
| 5,737,519 | A | 4/1998 | Abdelnour et al. |
| 5,748,495 | A | 5/1998 | Arita et al. |
| 5,832,410 | A | 11/1998 | Lin et al. |
| 5,832,411 | A | 11/1998 | Schatzmann et al. |
| 5,835,724 | A | 11/1998 | Smith |
| 5,861,303 | A * | 1/1999 | Barshter et al. ............ 435/266 |
| 5,865,718 | A | 2/1999 | Chan |
| 5,865,991 | A | 2/1999 | Hsu |
| 5,905,570 | A | 5/1999 | White et al. |
| 5,925,240 | A * | 7/1999 | Wilkins et al. ............... 210/88 |
| 5,966,683 | A | 10/1999 | Millett et al. |
| 5,970,426 | A | 10/1999 | Mandel et al. |
| 5,976,466 | A | 11/1999 | Ratner et al. |
| 5,993,662 | A | 11/1999 | Garr et al. |
| 6,012,152 | A | 1/2000 | Douik et al. |
| 6,023,223 | A | 2/2000 | Baxter, Jr. |
| 6,042,788 | A | 3/2000 | De Wit et al. |
| 6,061,603 | A | 5/2000 | Papadopoulos et al. |
| 6,074,539 | A | 6/2000 | Deininger et al. |
| 6,099,735 | A * | 8/2000 | Kelada ........................ 210/652 |
| 6,123,820 | A | 9/2000 | Bergkuist et al. |
| 6,208,940 | B1 | 3/2001 | Kram et al. |
| 6,236,941 | B1 | 5/2001 | Kram et al. |
| 6,245,224 | B1 | 6/2001 | Enoki et al. |
| 6,290,908 | B1 | 9/2001 | Fukunaga et al. |
| 6,305,944 | B1 | 10/2001 | Henry et al. |
| 6,317,639 | B1 | 11/2001 | Hansen |
| 6,317,694 | B1 | 11/2001 | Kram et al. |
| 6,332,110 | B1 | 12/2001 | Wolfe |
| 6,356,205 | B1 | 3/2002 | Salvo et al. |
| 6,370,448 | B1 | 4/2002 | Eryurek |
| 6,387,329 | B1 | 5/2002 | Lewis et al. |
| 6,389,331 | B1 | 5/2002 | Jensen et al. |
| 6,398,930 | B1 | 6/2002 | Fukunaga et al. |
| 6,444,172 | B1 | 9/2002 | Fukunaga et al. |
| 6,458,257 | B1 * | 10/2002 | Andrews et al. ............ 204/263 |
| 6,523,426 | B1 | 2/2003 | Vincent et al. |
| 6,560,543 | B1 | 5/2003 | Wolfe et al. |
| 6,591,166 | B1 | 7/2003 | Millett et al. |
| 6,607,668 | B1 * | 8/2003 | Rela ........................ 210/321.6 |
| 6,625,548 | B1 | 9/2003 | Babel |
| 6,626,042 | B1 | 9/2003 | Havlena |
| 6,670,810 | B1 | 12/2003 | Duncan et al. |
| 6,677,861 | B1 | 1/2004 | Henry et al. |
| 6,738,728 | B1 | 5/2004 | Jacquez |
| 6,798,347 | B1 | 9/2004 | Henry et al. |
| 6,836,737 | B1 | 12/2004 | Petite et al. |
| 6,839,597 | B1 | 1/2005 | Hattori et al. |
| 6,845,336 | B1 | 1/2005 | Kodukula et al. |
| 6,915,211 | B1 | 7/2005 | Kram et al. |
| 6,936,156 | B1 | 8/2005 | Smith et al. |
| 6,954,701 | B1 | 10/2005 | Wolfe |
| 2001/0020195 | A1 | 9/2001 | Patel et al. |
| 2001/0053992 | A1 | 12/2001 | Eto et al. |
| 2002/0019725 | A1 | 2/2002 | Petite et al. |
| 2002/0023479 | A1 | 2/2002 | Burge et al. |
| 2002/0130069 | A1 | 9/2002 | Moskoff |
| 2002/0133270 | A1 | 9/2002 | Hung et al. |
| 2002/0142477 | A1 | 10/2002 | Lewis et al. |
| 2003/0177851 | A1 | 9/2003 | Kent et al. |
| 2004/0006513 | A1 | 1/2004 | Wolfe |
| 2004/0138840 | A1 | 7/2004 | Wolfe et al. |
| 2004/0144163 | A1 | 7/2004 | Kram et al. |
| 2005/0066711 | A1 | 3/2005 | Discenzo |
| 2005/0247114 | A1 | 11/2005 | Kahn et al. |
| 2005/0251366 | A1 | 11/2005 | Kahn et al. |
| 2005/0251367 | A1 | 11/2005 | Kahn et al. |
| 2006/0020427 | A1 | 1/2006 | Kahn et al. |

FOREIGN PATENT DOCUMENTS

| | | |
|---|---|---|
| GB | 2131169 A | 6/1984 |
| WO | 01/80494 | 10/2001 |

OTHER PUBLICATIONS

M. Kahn et al., Copending U.S. Appl. No. 10/840,639, Fluid Monitoring Systems and Methods with Data Communication to Interested Parties, filed May 7, 2004 (unpublished).

M Kahn et al., Copending U.S. Appl. No. 10/840,650, Multi-Sensor System for Fluid Monitoring with Selective Exposure of Sensors, filed May 7, 2004 (unpublished).

Richard B. Brown, *Solid-State Liquid Chemical Sensor Testing Issues*, Proceedings of the International Test Conference, 2000, p. 1135, IEEE.

Hyo Jung Yoon et al., *Solid-state ion sensors with a liquid junction-free polymer membrane-based reference electrode for blood analysis*, Sensors and Actuators B 64, 2000, pp. 8-14, Elsevier.

Water Recirculation Project, Northwest Fisheries Science Center National Marine Fisheries Service (NOAA), Northwest Fisheries Science Center, http://www3.nwfsc.noaa.gov/recirc, Internet document dated Oct. 16, 2002, 3 pages.

NWFSC Water Recirculation Project: Data Acquisition and Web Display, Northwest Fisheries Science Center, http://www3.nwfsc.noa.gov/recirc/scripting.html, Internet document dated Oct. 16, 2002, 3 pages.

Thomas M. Scott and Michael B. Rust, *A Computer Automated Cold Water Recirculating System For Aquaculture Research*, copy of paper presented at Success and Failures in Commercial Recirculating Aquaculture Conference, Jul. 19-21, 1996, Virginia Tech. University.

Remote Measurement Systems, Case Studies—Fisheries/Aquaculture Remote Measurement Systems Inc., http://www.measure.com/casestud-fish.html, Internet document dated Oct. 16, 2002, 4 pages.

Soreide, et al., *Mosaic access to realtime data from the TOGA-TAO array of moored buoys*, Internet document from web site Equatorial Pacific, dated Oct. 16, 2002, pp. 1-8.

Michael Franklin and Stan Zdonik, "*Data In Your Face*": Push Technology in Perspective, SIGMOD Record, vol. 27, Issue 2, Jun. 1998, pp. 516-519.

A.D. McKinnon and C.W. Hubbard, *Automating Communications with and Developing User Interfaces for Remote Data Acquisition and Analysis Systems*, IEEE Transactions on Nuclear Science, vol. 44, No. 3, pp. 1062-1064, Jun. 1997.

SMART Plant Works: Outsourcing ASP-Style, undated, 4 pages.

The Aqua Trend Network—The New Standard In High Speed Data Management (Product Brochure), 2000, 4 pages, Hach Company.

WebHMI—Web-Based Real-Time Autonation Software (Product Brochure), 2002, 4 pages, Iconics, Inc.

Wonderware Suite Voyager 2.0—Plant Intelligence Portal (Product Brochure), Jul. 2003, 5 pages, Invensys Systems, Inc.

Ingo Cyliax, "*Remote Internet Data Logging and Sensing*", Circuit Cellar Magazine, Embedded PC, PC/104 Quarter 104, Nov. 1997, pp. 53-59.

Sanz-Bobi, M.A., et al., "*Control and diagnosis of water chemistry in the water-stream and water make-up in a fossil fuelled power plant*," Electrical Power & Energy Systems, vol. 16, No. 4, 1994, pp. 251-258.

Asakura, Y., et al., "*Structural Material Anomaly Detected System Using Water Chemistry Data*," J. Nuclear Sci. & Tech., 29(11), Nov. 1992, pp. 1120-1126.

Igarashi, H., et al., "*Development of Water Chemistry Diagnostic System for BWRs Using Fuzzy Reasoning*," J. Nuclear Sci. & Tech., 31(10), Oct. 1994, pp. 1023-1037.

Kneile, "*Writing More Information Out of Plant Data*" Chemical Engineering, Mar. 1995, pp. 110-116.

Remote Measurement Systems, "Posting Real-Time Measurement to the Web", Home Energy, Internet document from web site Posting Real-Time Measurements to Web Page, dated Oct. 16, 2002, pp. 1-5.

EPRI chemWORKSTM Users Manual vols. 1 and 2, 1995, Electric Power Research Institute, Inc. (EPRI).

Sensicore, the new math for water profiling (Product Brochure). May 2004, 4 pages, Sensicore, Inc.

Crossbow-water, Internet document retrieved on Mar. 27, 2004, retrieved from http://www.crossbow-water.com/os.html, 45 pages.

WaterTrax Agency Service (brochure), 2003, 2 pages, retrieved from the Internet on Aug. 12, 2005 at http://www.watertrax.com/pdf/WaterTrax_Agency_Service.pdf.

WaterTrax Utility Service (brochure), 2003, 2 pages, retrieved from the Internet on Aug. 12, 2005 at http://www.watertrax.com/pdf/WaterTrax_Utility_Service.pdf.

* cited by examiner

FLUID TREATMENT APPARATUS WITH INPUT AND OUTPUT FLUID SENSING

CROSS REFERENCE TO RELATED APPLICATIONS

This application is related to U.S. Patent Application entitled "Monitoring Systems and Methods for fluid Testing", Ser. No. 10/840,628, U.S. Patent Application entitled "Fluid Monitoring Systems and Methods with Data Communication to Interested Parties", Ser. No. 10/840,639, and U.S. Patent Application entitled "Multi-Sensor System for Fluid Monitoring with Selective Exposure of Sensors", Ser. No. 10/840,650, all filed May 7, 2004, the contents of each being incorporated herein by reference.

BACKGROUND

1. Field of the Disclosure

The disclosure relates generally to sensor systems and methods for fluid monitoring. More particularly, the disclosure relates to sensor systems and methods for wide distribution of sensors and on-line monitoring of fluids (e.g., water).

2. Background Information

The quality and surety of drinking water is of ever increasing importance throughout the world. Contaminants, such as toxins, biological agents, inorganic compounds and particulate matter that enter a contiguous water distribution system either naturally, or are purposely placed there as a terrorist act, have the capacity to diminish the quality of the water to an unacceptable level, and each member of the population, whether human or other life form, is at risk of exposure to water of such substandard quality. Water can become contaminated at its source, whether that be from wells, rivers, reservoirs or treatment plants, or can become contaminated once the water is introduced into a contiguous water distribution system. Regardless of its source or type, water quality degradation can have a significant detrimental health affect that can sometimes be seen quickly and often times is not recognized or detected for years or even decades.

Measures have been taken for monitoring the quality of drinking water including placing monitors at various points in the source water, in water treatment plants, and/or at selected distribution points of water distribution pipe networks within a region of a water authority, for instance. The selection, access to appropriate sites and acquisition/placement of water quality monitoring components and systems tend to be labor intensive and costly for a regional or multi-regional water authority to implement. This high cost and significant on-going maintenance requirement for remote monitoring systems has severely limited the number of locations monitored and is the primary reason that most testing is performed on a low-volume basis by bringing "grab samples" of water back to a laboratory for testing. Several considerations are at issue: the density of testing (i.e., how many locations in a reservoir or within a city should be monitored to protect the population from exposure, e.g., each city block or within a 5-block, 10-block or 20-block area); the frequency of testing (e.g., whether taking a grab sample once a month for a given location is sufficient to protect the population); and the time delay in receiving "actionable" data about contamination that may already be affecting tens of thousands of people by virtue of the testing being done on a non-continuous basis.

Additionally, many water quality sensors create false positives, or false negatives, in determining substandard water conditions. These false positives can be expensive insofar as they require investigation and repair of a sensor node and could even result in the shut-down of a water distribution system section or, more commonly, an alert that disrupts a population's use of water. False negatives can be even more costly if hazardous conditions are not timely detected.

Further, the need for sharing of water quality measurements, particularly in real time, is of ever increasing importance. Not only do regional water authorities need real time measures of water quality to improve system performance, multiregional (e.g., county, province, state or national) water authorities desire original data whether in the form of raw data or analyzed results of the water quality in a particular water distribution region. This information can be used to assure compliance with water quality standards, for instance. This information is generally provided by the regional water authorities, which may not have sufficient incentives to provide completely candid reports. Also, in these uncertain times, real time awareness of possible or actual sabotage can be of critical importance, if only to provide assurance to the general population that the water supply is safe.

Thus, there is a need for improvements in sensing whether a municipal, industrial or even home water purification/treatment system is operating properly and providing water of a certain quality. This can be particularly important when a municipality places water treatment equipment in remote locations to selectively or more cost effectively treat water instead of treating the entire bulk water at the municipality.

Finally, there is a need to confirm the purity and surety of water sold as pure from a commercial water treatment system in order to verify manufacturers claims of providing pure water.

SUMMARY OF DISCLOSURE

Various embodiments of the present disclosure address these as well as other concerns raised by the state of the art.

For instance, the present invention can include a system for monitoring a fluid that includes monitoring, identifying, confirming and then reporting a detection event. Several embodiments of monitoring means for monitoring a fluid and generating a variable based on the monitoring, and for generating a preliminary identifier if the variable is indicative of a detection condition, are disclosed. Similarly, several embodiments of confirming means for testing the fluid and for determining whether the detection condition has occurred based on new data, are also disclosed. Additionally, several embodiments of reporting means for reporting the detection condition to a remote communication device, if the confirming means determines that the detection condition has occurred, are disclosed.

More specifically, embodiments of the present invention can be in the form of a system for monitoring a fluid, which includes a first sensor configured to be exposed to a fluid and a second sensor configured to be exposed to the same fluid sample. Such a system may also include a processing unit coupled to the first sensor and the second sensor, the at least one processing unit being configured to (1) operate in conjunction with the first sensor to monitor the fluid, (2) generate a variable based on its monitoring, (3) generate a preliminary identifier if the variable is indicative of a detection condition, and (4) operate in conjunction with the second sensor to determine whether the detection condition has occurred based on new data. A communication unit can be configured to report the detection condition to a remote communication device if the processing unit confirms that the detection condition has occurred. The method being carried out by these means is also disclosed.

In another example, a system for monitoring a fluid can include a fluid treatment device; a first sensor configured to be exposed to pre-treatment fluid that enters the fluid treatment device; and a second sensor configured to be exposed to post-treatment fluid. The fluid treatment device can comprise for instance a filter housing, a filter, a water-softening device, a distillation device, a reverse-osmosis filtration device, or any combination thereof, as an example.

In another example, a multi-sensor apparatus for monitoring a fluid is also disclosed. The multi-sensor apparatus can include, for instance, a substrate; a plurality of sensors attached to the substrate, each sensor configured to be exposed to a fluid; and one of several means for selectively exposing a particular sensor of the plurality of sensors to the fluid, and their equivalents. The exposing means can include, for instance, a membrane attached to a surface of the substrate, the membrane covering the plurality of sensors; and a plurality of heating elements attached to the membrane, a given heating element being positioned proximate to a given sensor, wherein each heating element is selectively operable to generate an opening in the membrane, thereby allowing a particular sensor positioned proximate to the opening to be exposed to the fluid. Alternatively or additionally, the exposing means can include a housing member in which the substrate is disposed, the housing member having an aperture in a wall thereof configured to allow a sensor to be exposed to a fluid; a seal arranged adjacent to the aperture and positioned between a surface of the substrate and a surface of the housing, thereby sealing the substrate against the housing; and an actuator for moving the substrate to selectively locate a individual sensor or group of sensors to a region of the aperture such that the individual sensor or sensor group is exposed to the fluid. In still another embodiment, the exposing means can be in the form of at least one cover membrane attached to a surface of the substrate, the at least one cover membrane covering the plurality of sensors; and a mechanical member for selectively displacing the at least one cover membrane in a region proximate to an individual sensor or sensor group to allow the sensor or sensor group to be exposed to a fluid; and an actuator for providing relative motion between the substrate and the mechanical member to allow the mechanical member to selectively displace the at least one cover membrane.

Sensor units in accordance with these aspects of the disclosure can monitor, identify, confirm and report detection events on a continuous or intermittent (e.g., periodic) basis to thereby reduce the incidence of either or both of false positives and false negatives.

Sensor systems in accordance with these aspects of the disclosure can provide a wide and potentially random distribution of sensor sites throughout a water distribution system at identifiable locations, potentially at final fluid output points (e.g., water facets) at the end user locations, establishing a potentially larger panel of monitoring sites than might otherwise be achievable within a similar level of expense. This is particularly true in circumstances where end users voluntarily pay for and install sensors units, providing advantages for themselves at the same time advantages are made available to water monitoring entities and the general public. The potential for large panels of distributed sensor sites increases the ability for water authorities to detect, trace and/or isolate sources of problems affecting water quality within a water quality monitoring system.

BRIEF DESCRIPTION OF THE DRAWINGS

The present disclosure will now be explained with reference to exemplary embodiments illustrated in the accompanying drawings to which the invention is not necessarily limited. Various advantages and other attributes of the invention will be identified or become apparent with respect to various specific embodiments, but not all embodiments within the scope of the present invention will necessarily include or have identified advantages or attributes. The scope of the invention should be determined based on recitations contained in the claims, and equivalents thereof, rather than reliance on advantages and attributes not positively recited in the claims. Further, although the term "invention" has been used in the singular, it should be recognized that more than one independent and/or distinct invention may be presented in the disclosure and claims.

DETAILED DESCRIPTION OF EXEMPLARY EMBODIMENTS

Figure 1A:
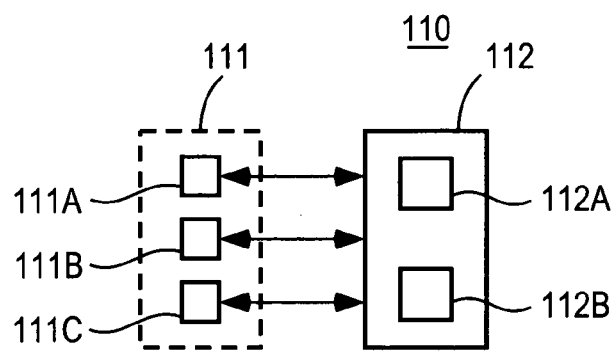
FIG. 1A is a block diagram of an exemplary embodiment of a sensor unit in accordance with an embodiment of the present disclosure.

For purposes of this document, the following should be understood. The term "water quality" generally relates to measures of various aspects of water or other fluids and fluids that tend to indicate the usefulness of or danger posed by a fluid including but not limited to the measure of various chemicals, chemical profiles, presence of biological agents and/or life forms, toxins, other organic and inorganic contaminants, and particulates, etc. For instance, although water distribution systems are a focus of several embodiments of the present invention, it is also possible that aspects of the present invention can be applied to monitor any fluid (gas or liquid) including those present in a distribution system, reservoir or feed source in need of monitoring. The term "confirm" should be understood to mean that additional evidence or support by another indication has been determined based on additional information, which can be of the same or a distinct type relative to the data leading to the original indication. "Distribution system" includes any system of fluid distribution (including air distribution systems such as, for example, air ducts), which in the case of water distribution, currently commonly manifest themselves as contiguous systems of pipes and/or systems of reservoirs, channels, pipes and treatment plants, but also can include less typical distribution channels such as container water, well water within a watershed or a water table, and even large bodies of water, oceans, rivers, streams and/or tributaries, or virtually anything wherein a fluid can flow from one point in the system to another, such as movement of water from one layer to another layer within a single body of water, a hallmark of which is the ability to identify the location of and communicate with sensor units within the water distribution system. Also, the phrase "same sample of fluid", "the fluid" and the like should be understood to mean any quantity of the fluid wherein the same or similar conditions are likely to exist. For example, for broad measures such as pH in a body of non-static water, all of a large pool or reservoir might be the same sample, whereas for detecting trace elements or alarming conditions, a water sample might mean only a few milliliters. The term "measuring" is not limited to embodiments wherein a numeric value or other analog or digital value is generated, but rather includes sensors and sensor elements that simply output a defined signal when a threshold (either an upper or a lower or both) is crossed. A sensor unit includes one or more sensors, sensor elements and/or sensor groups within a housing or located at a site, and includes processing and/or communication components. A sensor is a device designed to sense a parameter or parameters of a fluid and outputs a signal, typically to a processor. A sensing element is an element that forms part of a sensor and actually performs the measurement. The sensing elements of a sensor can be associated or coordinated in some fashion to perform monitoring and detection functions as a group, perhaps to determine a chemical profile of a sample. A sensor component is a generic term meaning any one of a sensor unit, sensor, or sensing element. A processing unit is a generic term meaning one or more processing units programmed at a software, firmware or hardware level, including, for example, ASIC (application specific integrated circuit). A processing unit can be multiplexed to multiple sensors or dedicated to a single sensor.

Sensors

Exemplary sensors can be selected to include any form of fluid measuring sensors, such as water quality measuring sensing elements including sensing elements for determining water temperature, water pressure, the presence or absence of any number of specific chemicals, chemical profiles and/or classes of chemicals such as for example and without limitation free chlorine ($Cl^-$), hypochlorous acid (HOCl) and hypochlorite ions ($OCl^-$), ion concentration, pH, carbon dioxide ($CO_2$), water hardness (e.g., $Ca^{2+}$), carbonate ($CO_3^{2-}$), monochloromine ($NH_2Cl$), dichloramine ($NHCl_2$), trichloramine ($NCl_3$), ammonium, nitrite, nitrate, fluoride, and/or chemical profiles, as well as determining water purity, clarity, color and/or virtually any other measurable or detectable parameter of interest with respect to water or any other fluid. Some such sensors are described in copending U.S. patent application Ser. No. 10/657,760 ("Method and Apparatus for Quantitative Analysis"), the entire disclosure of which is incorporated herein by reference. Such sensors can be used to monitor not only liquids, but also, with appropriate calibration, gases (e.g., air) as well. Such sensors can include one or more of, for example, electrodes and ion-selective membranes acting as ion-selective electrodes (ISEs), amperometric and potentiometric sensing elements that may or may not have electrode coatings on the electrode surfaces, conductivity sensing elements, temperature sensing elements, oxidation-reduction potential sensing elements, reference electrodes, oxygen sensing elements, immunosensors, DNA probes (e.g., hybridization assays with oligonucleotides) comprising appropriate coatings on electrode surfaces and a wide variety of optical sensors, to name a few. Other suitable sensor devices include those disclosed in U.S. Pat. No. 4,743,954 ("Integrated Circuit for a Chemical-Selective Sensor with Voltage Output") and U.S. Pat. No. 5,102,526 ("Solid State Ion Sensor with Silicone Membrane"), the disclosures of which are incorporated herein by reference.

Sensors for use in systems disclosed herein, such as those disclosed in copending U.S. patent application Ser. No. 10/657,760, U.S. Pat. No. 4,743,954, and U.S. Pat. No. 5,102,526, for example, can be fabricated using known lithographic, dispensation and/or screen printing techniques (e.g., conventional microelectronics processing techniques). Such techniques can provide sensors having sensing elements with micro-sized features integrated at the chip level, and can be integrated with low-cost electronics, such as ASICs (applications specific integrated circuits). Such sensors and electronics can be manufactured at low cost, thereby enabling wide distribution of such sensors to various entities, including private entities.

Exemplary sensors can be fabricated on silicon substrates or can be fabricated on other types of substrates such as, for example, ceramic, glass, $SiO_2$, or plastic substrates, using conventional processing techniques. Exemplary sensors can also be fabricated using combinations of such substrates situated proximate to one another. For example, a silicon substrate having some sensor components (e.g., sensing elements) can be mounted on a ceramic, $SiO_2$, glass, plastic or other type of substrate having other sensor components (e.g., other sensing elements and/or one or more reference electrodes). Conventional electronics processing techniques can be used to fabricate and interconnect such composite devices.

Also, a variety of other sensors, whether commercially available or not including those not yet developed, could be used within the system disclosed herein. While novel sensor units comprising various sensors are disclosed herein, other novel aspects of the present disclosure remain novel regardless of the form of sensor units. With regard to monitoring of gases such as air, any suitable sensor for detecting a target species can be used, such as, for example, electrochemical gas sensors including electrochemical sensors for detecting hydrogen cyanide as disclosed in U.S. Pat. No. 6,074,539, the entire contents of which are incorporated herein by reference.

Exemplary Monitor, Confirm and Report Systems

In one embodiment of the present disclosure shown in FIG. 1A, a system for monitoring water quality (or quality of any fluid) (330 in FIG. 3) can include a sensor unit 110 that includes a first sensor 111A and an associated processing unit 112A acting as a monitoring means for monitoring a fluid and generating a variable based on the content of a fluid. This processing unit 112A can be housed in a module 112 along with a communication unit 112B. This first sensor 111A either upon the detection of a quality in the fluid or by the measured or calculated variable associated with the fluid crossing a threshold, for instance, can generate a preliminary identifier if the variable is indicative of a detection condition. For instance, if the pH level (as the variable) or other water quality parameter rises too high or low, or the water pressure as measured by an incorporated pressure monitor drops below a threshold for instance, a preliminary identifier (e.g., a flag or a signal) is generated in this exemplary system. This preliminary identifier can trigger a second sensor 111B to begin measuring the same variable or a different variable, or to output a continuously measured result. The processing unit 112A can comprise a single processing unit or multiple processing units.

Alternatively, the second sensor 111B can be run in tandem with the first sensor 111A for testing the same sample of fluid a second time either using the same test or a different test that also is indicative of a detection condition. The results of the measures or tests are output from the processor as a confirmed result when they agree. The second sensor 111B and the processing unit 112A act as a confirming means for the first sensor or monitoring means 111A.

Alternatively, the second sensor 111B can be in the form of the first sensor 111A that is recalibrated for the second test.

Upon a positive result from the first sensor 111A in conjunction with the processing unit 112A (acting together as monitoring means) and a positive result from the second sensor 111B (or more sensors) in conjunction with the processing unit 112A (together acting as confirming means), the detection condition is communicated or reported by a communication unit 112B (acting as reporting means) to a remote communication device and/or a local indicator (e.g., a light or other form of alert on the sensor unit housing). Information regarding fluid measurement results can also be displayed on an optional display (e.g., located on the sensor unit housing). This form of sensor unit 110 thereby eliminates many false positives insofar as before a detection condition is reported, it is confirmed.

Also, more than one sensor can act as either the first and/or second sensor 111A, 111B to provide redundancy of tests or measures. In this way, if one sensor fails, another sensor acting in the same capacity acts as a back-up to reduce the chances of a false negative. Whether through detection of false positives or false negatives, or other means, a defective sensor or other sensor component can be deactivated by a processing means, for instance by simply not supplying power or not processing output from the defective sensor component.

As illustrated in the exemplary embodiment of FIG. 1A, the sensors in a sensor unit 110 can take the form of a first sensor 111A and a second sensor 111B and even more sensors 111C as circumstances warrant. Such sensors can collectively be referred to as a sensor group, which can also simply be referred to as sensor 111. Sensors of a sensor group may be physically configured together as a unit, but this is not necessary. For instance, the third sensor 111C can be provided to serve as part of the confirming means, thereby allowing the processing unit 112A to determine whether the detection condition has occurred based on a majority voting approach using data from the first sensor 111A, the second sensor 111B and the third sensor 111C, e.g., each sensor 111A–111B gets one vote or a weighted vote perhaps in the form of an analog or digital signal, and the condition indicated by a majority of such votes is reported to a remote communication device or local indicator. The third sensor 111C (or any number of additional sensors) can act as back-up sensors, or be used to further reduce false positives and/or false negatives using a majority voting technique. Such sensors can include, for example, electrodes and ion-selective membranes acting as ion-selective electrodes (ISEs), amperometric and potentiometric sensing elements that may or may not have electrode coatings on the electrode surfaces, conductivity sensing elements, temperature sensing elements, oxidation-reduction potential sensing elements, oxygen sensing elements, immunosensors, DNA probes (e.g., hybridization assays with oligonucleotides) comprising appropriate coatings on electrode surfaces and a wide variety of optical sensors, to name a few.

Figure 1B:
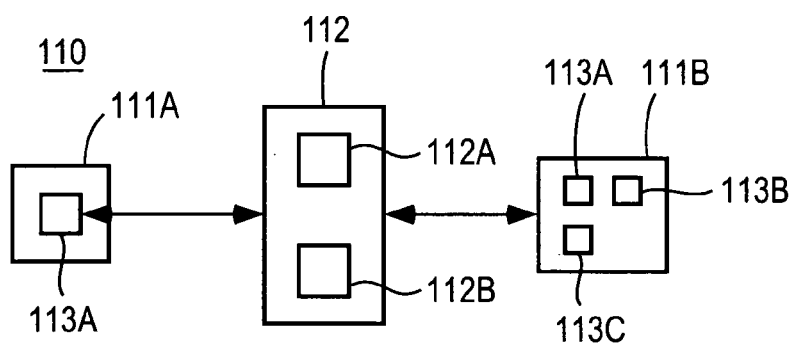
FIG. 1B is a block diagram of another exemplary embodiment of a sensor unit in accordance with another embodiment of the present disclosure.
Figure 1C:
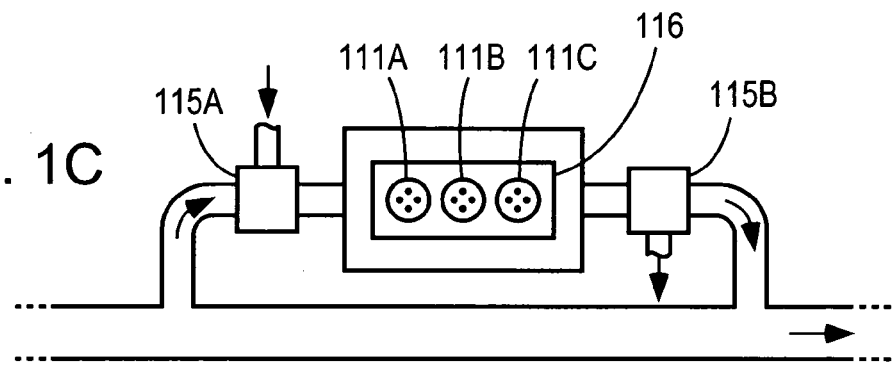
FIG. 1C is an illustration of an exemplary embodiment of a sensor unit.

The sensors 111A–111C can each be made up of a single sensor element 113A, a plurality of sensor elements 113A–113C, perhaps for redundancy, or one or more sensor groups, as shown in FIG. 1B. The sensor elements 113A–113C can be of the same type or of different types to measure, for example, the same parameters for sake of redundancy and greater accuracy, or measure different aspects of a chemical or biological profile or signature. The first sensor 111A and/or the second sensor 111B can, for instance, can respectively comprise a sensing element 113A capable of measuring an ion content and a sensing element capable of measuring a chlorine content. More generally, the sensors 111A–111C can comprise at least one of an ion-selective sensing element, an amperometric sensing element, a potentiometric sensing element, a conductivity sensing element, a temperature sensing element, an oxidation-reduction potential sensing element, a chlorine sensing element, an oxygen sensing element, an immunosensor, a DNA probe and an optical sensor. The sensors 111A–111C can be provided on distinct substrates, or be provided on the same substrate 116, as shown in FIG. 1C.

The processing unit 112A and the communications unit 112B act as the reporting means for reporting a confirmed event based on processed data from the first and second sensors 111A, 111B, or any number of a plurality of sensors 111 in a sensor unit 110.

In one exemplary embodiment, each of the plurality of sensors 111A–11C is of the same type for monitoring the same parameters or profile of the fluid. In this way, if a first sensor 111A indicates false positives, the second sensor 111B would act to confirm or not confirm any detection event thereby reducing the number of reported false positives. Alternatively, the first sensor 111A may be of a more robust nature but perhaps lower sensitivity or have a broader range of detectable conditions, whereas the second sensor 111B might be more sensitive or of a limited detection range or of a special type to detect a specific substance (one-shot sensors) and under these circumstances might be invoked, for instance, only when the first sensor 111A generates a preliminary identifier indicative of a detection condition. For example, where the first sensor 111A has an array of sensing element of the types noted above, and generated a profile reading suggestive of cyanide, for example, a one-shot sensor that can specifically detect cyanide or detect smaller amounts of cyanide, can be activated or exposed. The second sensor 111B, being more sensitive or more be capable of more accurately identifying a given detection condition, would then be better able to confirm the existence of a detection event with greater certainty.

The second sensor 111B could have at least one characteristic such as greater sensitivity, more specific sensitivity, or be able to detect secondary traits of a suspected substance indicated by the preliminary identifier. In the later case there might be a plurality of second sensors 111B each associated with a given, more specific test or measure of the quality of the fluid, and activated as a group or individually based on the information contained in the preliminary identifier. The second sensor 111B could, however, be the same type of sensor as the first sensor 111A in certain embodiments.

Further, the second sensor 111B can be coupled to a mechanism to change the fluid or its environment prior to detection by the confirmation sensor. For instance, a single sensor 111A can be utilized and, upon generating a preliminary identifier, a recalibration solution can be injected by pumps, valves, microfluidics or other means, onto the sensor, wherein the recalibration solution has a known, constant parameter measurable by the sensor 111A to recalibrate the sensor 111A for a subsequent measurement. Alternatively, a reagent can be introduced into the fluid, the reagent being specific to the detection condition to change the nature of the fluid in a controlled fashion to assist in identifying the constituents of the fluid that is causing the detection condition. Enough recalibration fluid or reagent could be supplied to last the expected life of the sensor 111A, or be in the form of a replenishable supply.

For instance, as illustrated in FIG. 1C, a fluid control device such as a valve 15A is located on the input side of a senor unit 110. The valve 115A could then toggle between allowing fluid from the distribution system into the sensor unit 110 and allowing a calibration fluid into the sensor unit 110. On the output side of the sensor unit 110, a similar fluid control device such as a valve 115B can be used to remove the calibration fluid as waste, if introducing it into the monitored fluid raises potential concerns or the output fluid control device can be omitted if allowing the fluid in the sensor unit 110 to rejoin the fluid in the distribution system does not raise concerns.

The single sensor 111A may be thereby recalibrated by exposure to recalibration agent or the like, but alternatively can be simply electrically recalibrated by normalizing its response based on background conditions.

Figure 3:
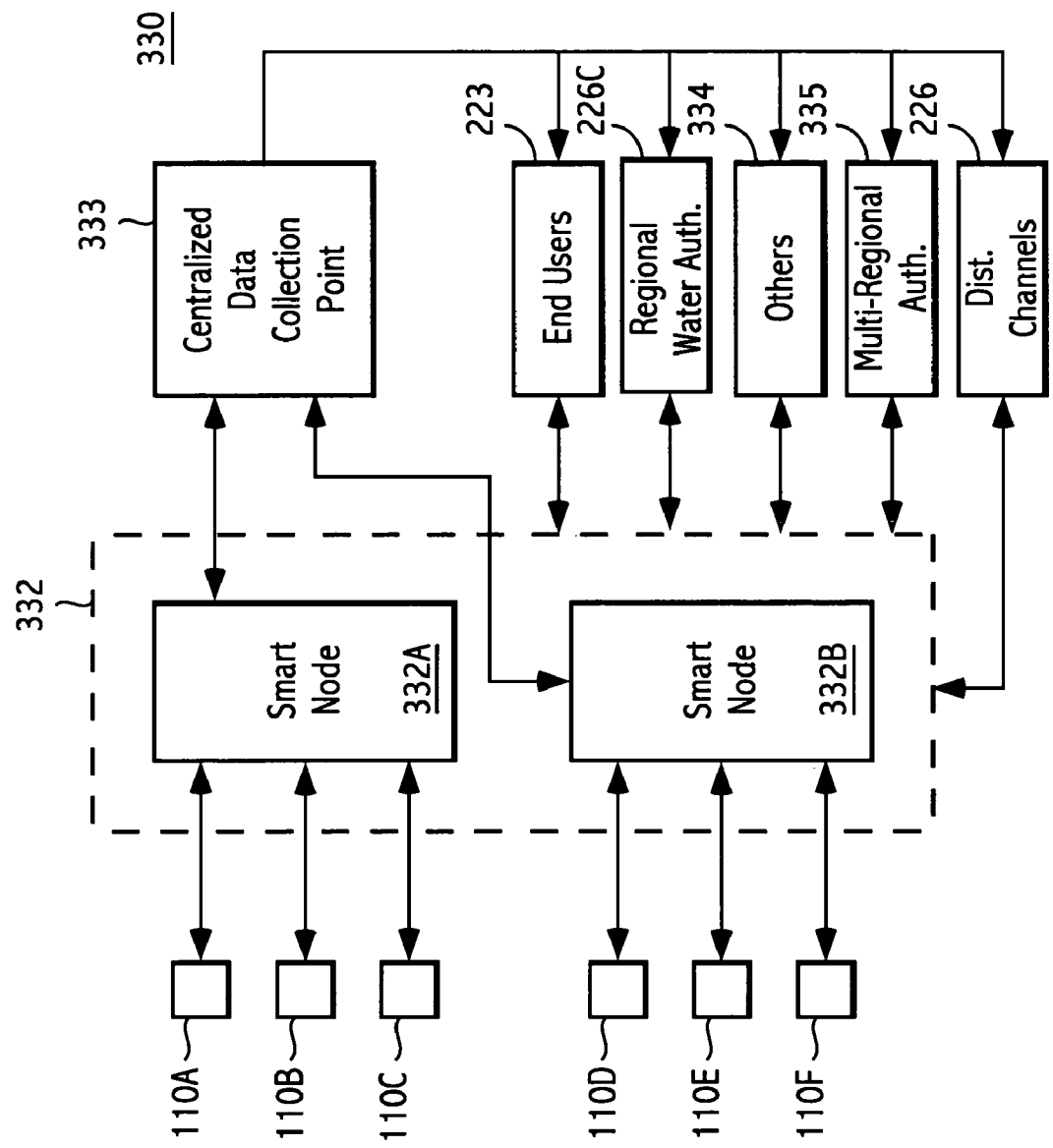
FIG. 3 is a block diagram of an exemplary data collection network, data distribution network and data analysis network in accordance with aspects of the present disclosure.

As perhaps easier to understand with respect to the fluid monitoring system of FIG. 3, one sensor can be used to calibrate another sensor. More specifically, in a network situation, a new sensor placed into the system could be used to calibrate older sensors that might have been subject to calibration drift over time. The old and new sensors would detect the same fluid either in the fluid distribution system or as reagents or calibration solutions, and the new sensor readings would be used to adjust or calibrate the older sensor. The sensors ought to be neighboring, or relatively remote, as long as the fluid being used is substantially the same in relevant ways, e.g., has the same pH, is taken from a small sample or a sample likely to have the same or uniform characteristics. The recalibration sensor merely has to be measuring a parameter that is similar enough to the sensor to be recalibrated to make the recalibration effective.

The recalibration sensor and the sensor to be recalibrated can communicate through any suitable means for reporting, such as described, for example, in the different embodiment disclosed herein, to a recalibration circuit. The recalibration circuit may be in the form of programming in a computer at a centralized location, such as the smart nodes 332 or centralized data collection points 333 as shown in FIG. 3, or a circuit or ASIC processor units in a module 112 such as disclosed in the embodiments of FIGS. 1 and 2. The recalibration circuit would have received, either through human input or by any suitable automatic means including the registration of a new or replacement sensor, an indication that the newer sensor, generally, would be the recalibration sensor, assuming that calibration drift of older sensors is a problem being addressed.

Further, once one sensor is recalibrated it can be used to calibrate the next in a network, for instance, to create a domino effect for recalibration of sensors measuring fluid having a relatively uniform measurement characteristic. For instance, an individual pipe with multiple sensors spaced along it can sequentially recalibrate the next sensor at a rate equal to fluid flow through the pipe.

The sensors 111A–111C can be any combination of the above and there may be a multiplicity of individual sensors, some or all of which may comprise a plurality of sensing elements. For instance, a sensor (e.g., sensor 111B in FIG. 1B) can have a plurality of sensing elements 113A–113C to detect multiple parameters within the fluid. Only three sensing elements 113A–113C are illustrated in FIG. 1B, but more than three could be employed. In this way, a sensor 111A can be used to identify chemical signatures or profiles within a fluid (e.g., potable water).

Figure 1D:
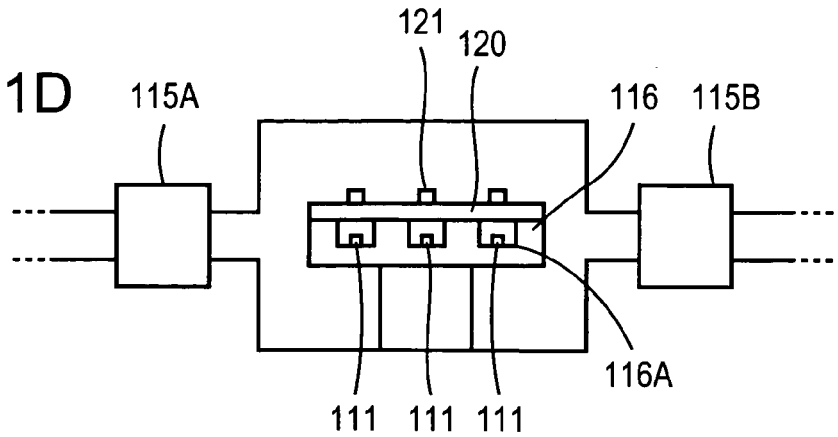
FIG. 1D is an illustration of another exemplary embodiment of a sensor unit.
Figure 1J:
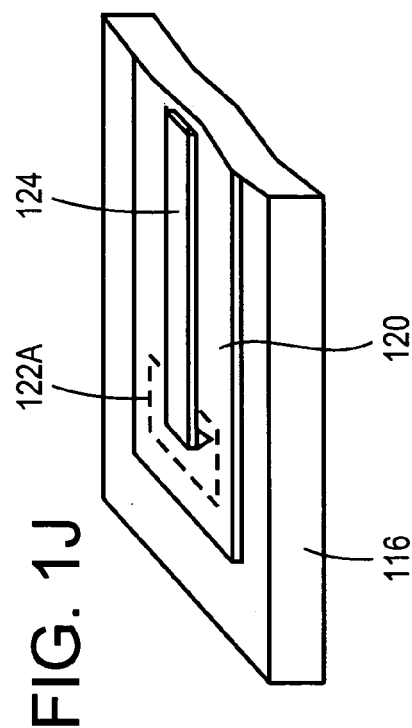
FIG. 1J is an illustration of another exemplary embodiment of a sensor unit.
Figure 1E:
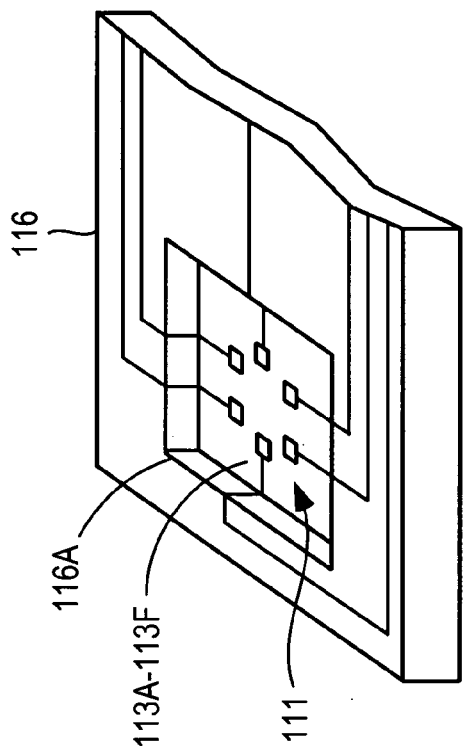
FIG. 1E is an illustration of another exemplary embodiment of a sensor unit.

A sensor 111A, such as shown schematically in the example of FIG. 1E can be made up of individual sensing elements 113A–113F. These sensing elements 113A–113F can be designed to identify different ranges of parameters within a fluid, specific chemicals or substances (e.g., compounds, contaminants) or identify different possible water quality measures, as tailored to the specific expected needs of the water quality monitoring system. Together, such sensing elements 113A–113F can provide a chemical profile of a fluid or can provide data indicative of fingerprints of particular substances (e.g., compounds, contaminants) or classes of substances (e.g., compounds, contaminants). The sensing elements 113A–113F may be mounted on a recessed surface, as shown in FIGS. 1D and 1E or they may be mounted on a non-recessed surface. The sensing elements 113 shown in the recesses 116A of FIG. 1D do not necessarily form a profile on the surface, as shown for emphasis in FIG. 1D, but may instead be co-planar with the surface. Electrical connections are mounted or formed on a substrate 116 in any or many known ways to connect the sensing elements 113A–113F to a processing unit 112A.

Whenever a plurality of sensor components (e.g., 111A–111C, 113A–113F) are incorporated into a sensor unit 110, they may each have a separate processing unit 112A and/or communication unit 112B, or may share common such components via a multiplexer or the like to reduce costs and communication overhead (bandwidth, power consumption, etc.). For instance, ASIC (applications specific integrated circuits) can be utilized to develop sensor units 110 of efficient design. These ASICs can be on a common substrate, or multiple substrates coupled together through electrical connections.

One or more sensors 111 can provide indications of event conditions on a number of bases, including one or more out-of-range events where measured parameters or profiles within a fluid exceed or deviate from a particular range and/or threshold either preprogrammed or downloaded into the sensor unit 110. The sensor units 110 can also provide detection of water profile parameters for comparison against water profile parameters either downloaded into the sensor units 110 or at smart nodes 332 or centralized data collection points 333, as explained in greater details with reference to FIG. 3, below. The detection of chemical fingerprints, signatures or profiles would be coupled to a database of potential chemical profiles for positive identification of even complex contaminants including biological agents and chemical toxins, for example. In this regard, such a database of potential chemical profiles can be stored locally (e.g., on-chip) in a memory interfaced to the processing unit 112A, or can be stored at one more remote locations for on-line access by the processing unit 112A and communication unit 112B. In either case, the database of potential chemical profiles can be updatable, and in the case of the local memory, the database of potential chemical profiles can be downloaded intermittently into the local memory. Suitable pattern recognition techniques can be used to compare data generated by the sensor unit(s) 110 with the database of potential chemical profiles to generate a potential identification event if there is a potential match with one or more stored chemical profiles.

Physical events, such as a breakage of a pipe might be detected through a pattern of sensor units 110 reporting readings that deviate from historic norms, for example, reduced water pressure compared to historic norms, thereby identifying the exact location or proximate location of the breakage. Also, temperature sensors could be utilized to normalize and scale temperature dependent detection mechanisms but also may be utilized to determine when water distribution systems are at risk of breakage through freezing temperatures.

The sensor unit 110 includes processing and communication units 112A and 112B. The communication capability of the sensor units 110 can include hardwired communication circuits wherein the unit is literally physically connected by wires to other communications devices or communication systems such as telephone lines, satellite or wireless communication devices, etc. The communication unit 112B may also impose information on a carrier for existing power lines within the building or even the power grid of a region. The imposed information signals would then be picked up by local communications devices for long-range communication over telephone lines, private or public networks, cellular communication networks, SMS (short message service) networks, satellites, etc. Additionally or alternatively, the communication unit 112B of an individual sensor unit 110 can include short-range wireless capabilities for communication with local alert and/or long-range communication devices such as telephones, private or public networks, cellular communication networks or satellite devices that may preexist or be installed for communication with a sensor unit 110. Such short-range wireless devices include communication devices utilizing unregulated spectrums using existing protocols such as Bluetooth. Alternatively, wireless LAN protocols such as dictated by IEEE Standard 802.11(b) or 802.11(g) could be used, as could long-range wireless devices for transmission to relatively distant stations such as at receivers located at the headquarters of regional water authorities. Other alternatives include communication devices 112B which utilize a pre-existing cellular network or wireless networks such as those used by alarm systems. The manner of communication might be dictated by external factors including availability, cost, robustness, efficiency, etc.

A network of sensor units 110 as described herein can be configured to communicate with a central communication device, e.g., a server, and/or sensor unit 110 can communicate with each other as a distributed network, using communication components known in the art. In this way, for example, a first sensor 111A can generate a preliminary identifier if it measures a water quality variable indicative of a detection event (e.g., low chlorine in a potable water system) and can trigger a neighboring second sensor 111B via the distributed network to make a confirmation measurement.

Finally, or in addition to, the communication unit 112B can include on-site alerts such as optical (indicator lights), audible alerts (e.g., alarm sounds), tactile (e.g., vibration of the unit) or can be interfaced to an appropriate control valve for simply shutting off the supply of fluid upon the detection of emergency events, for instance.

Packaging and Location

The sensor units 110 can be packaged and located in a variety of ways. For instance, they can be placed at the shut off valve located at the introduction of water supply into a house, business, industrial site or government site, for instance. Alternatively, they can be placed at each individual faucet or selected faucets where it is likely that the end user 23 might drink water or otherwise consume or cause fluids to be consumed. For instance, water filtration devices adaptable for attachment at the end of a faucet can be adapted to incorporate a sensor unit 110 and include both communication devices that communication with distant locations as well as integrally housed alerts either of an optical, audible or tactile nature. Also, sensor units 110 can be located at any desired points in a municipal water distribution system.

Filter Package Monitors

Figure 1H:
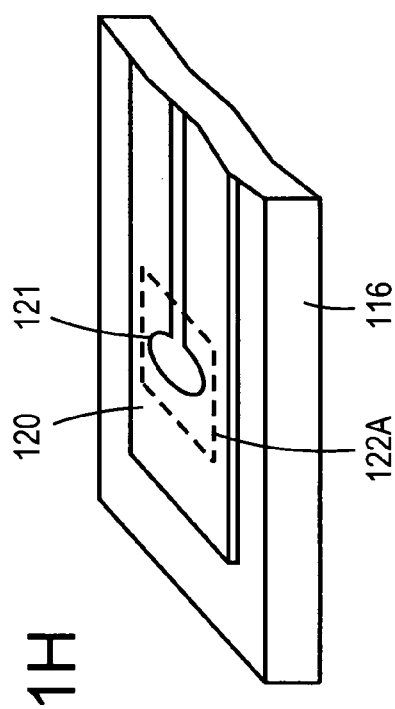
FIG. 1H is an illustration of another exemplary embodiment of a sensor unit.
Figure 1F:
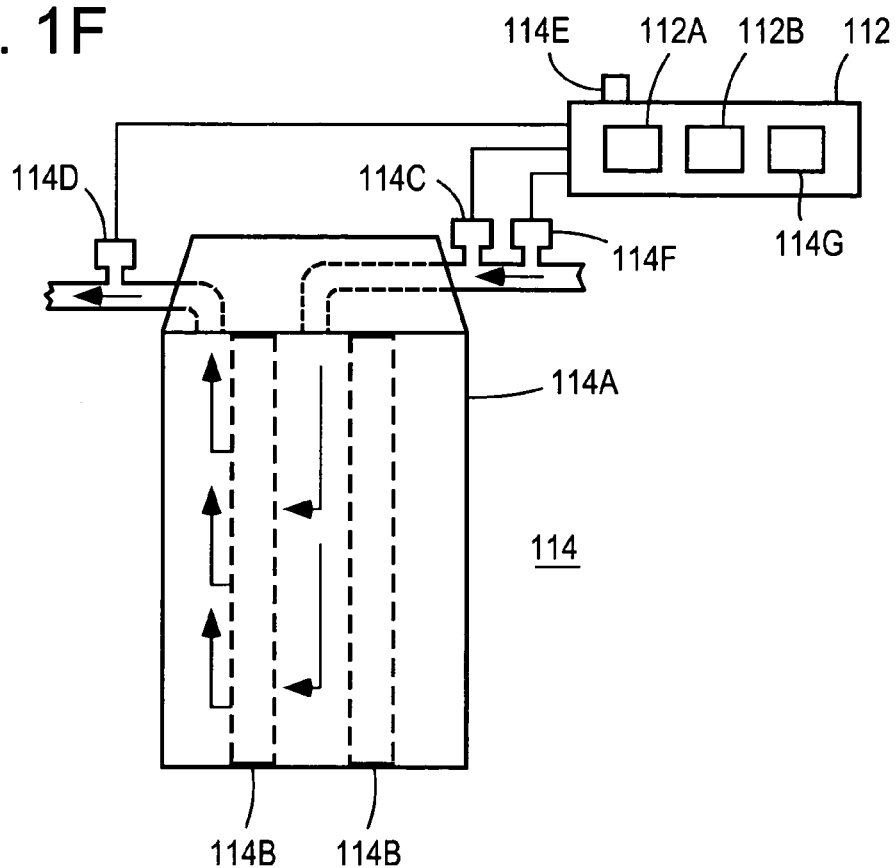
FIG. 1F is an illustration of another exemplary embodiment of a sensor unit.

One exemplary embodiment of the present invention combines a water filter and/or water treatment device with one or more sensor units 110. As illustrated in FIG. 1F, a system for filtering and monitoring a fluid includes a filter unit 114. The filter unit 114 includes a filter housing 114A for holding a filter 114B. A first, intake sensor 114C is configured to be exposed to fluid that enters the filter unit 114 (pre-filtering fluid, or more generally, pre-treatment fluid). A second, output sensor (post-filtering fluid) 114D is configured to be exposed to fluid filtered by the filter 114B (post-filtering fluid, or more generally, post-treating fluid). The first, intake sensor 114C can include a plurality of sensors 111A, 111B, 111C, etc., each of which can have one or more sensing elements 113A, 113B, 113C, etc., as can the second, output sensor 114D, such as described above. The individual sensors 111A, 111B, 111C, etc., can act as the monitoring and confirming means for each sensor 114C, 114D, depending on how they are connected and used by a processor 112A, or the intake or output sensing 114C, 114D can act as respective monitoring and confirming means (the roles being interchangeable) for fluid quality measures that are not effected by the filter 114B.

For instance, the first, intake sensor 114C can include an ion-selective sensing element capable of measuring an ion content and a chlorine sensing element capable of measuring a chlorine content. Likewise, the second, output sensor 114D can include an ion-selective sensing element capable of measuring an ion content and a chlorine sensing element capable of measuring a chlorine content. Moreover, each sensor 114C and 114D can comprise additional sensing elements, e.g., electrical conductivity and/or other sensing elements, capable of generating a suite of measurements that can provide particular measurements, which can be combined to generate a fluid-quality profile. For example, the sensors 114C and 114C can comprise at least one of an ion-selective sensing element, an amperometric sensing element, a potentiometric sensing element, a conductivity sensing element, a temperature sensing element, an oxidation-reduction potential sensing element, a chlorine sensing element, an oxygen sensing element, an immunosensor, a DNA probe and an optical sensor.

The filter unit 114 can further include a processing unit 112A coupled to the first and second sensor units 114C, 114D, the processing unit 112A being configured to compare measurement data generated by the first and second sensor units 114C, 114D.

The filter unit 114 can also include a communication unit 112B, either as part of or separate from the processing unit 112A, but coupled to the processing unit 112A. The communication unit 112B can be configured to communicate measurement results (e.g., raw and/or processed data) generated by the processing unit 112A to a remote communication device in the exemplary embodiment of FIG. 1C. It should be noted too that the processing unit 112A can be in the form of a first processing unit and a second processing unit, wherein the first processing unit is arranged with and coupled to the first sensor 114C, and wherein the second processing unit is arranged with and coupled to the second sensor 114D. The first and second processing units can be coupled together to achieve the desired measurement and comparison functions. Also, as with other embodiments described herein, sensor units 110 (whether or not packaged with a filter) can be monitored by a water treatment provider for the purpose of guaranteeing or certifying the quality of filtered and/or otherwise treated water. For example, a private water treatment company or a municipality can provide on-line monitoring of water filtration/treatment equipment at a delivery point (e.g., a home or business), and as part of its service, can guarantee or certify the quality of filtered and/or otherwise treated water. The water filtration/treatment equipment can be provided and/or installed by the monitoring entity or by a different entity. Further, one or more sensors placed at the water intake of a filter/treatment unit can be used to predict how long a treatment element (e.g., filter element) is expected to last based on loading capacity of that element and the amount of contaminants present in the intake water as measured by the sensor(s), and this information can be communicated on-line to the water treatment provider by any suitable method as disclosed herein.

As for packaging, the first and second sensor 114C and 114D can be attached to the filter housing 114A, but the filter 114B that filters the fluid can be replaceable without necessarily replacing the first and second sensors 114C, 114D depending on the particular embodiment. The sensors 114C, 114D can be designed to last the life of the filter unit 114, or be separately replaceable or replaceable with the filter 114B. In the latter case, it might be expedient to have the first and second sensor units 114C, 114D attached to or embedded in the filter 114B, such as shown in the exemplary filter unit 114' illustrated in FIG. 1G. In this regard, an appropriate interface, such as a waterproof plug, can be provided to couple the sensors 114C, 114D to the processing unit 112A.

In this way, the processing unit 112A is configured to generate an identifier to indicate a replacement condition for a filter 114B to be placed in the filter housing 114A based upon the comparison of the measurement data from the first and second sensor units 114C and 114D. An indicator 114E (e.g., a simple light, with or without a label, or an audible indicator) that indicates the replacement condition for the filter might be included as attached to or part of the filter housing 114A for instance, and/or the communication unit 1121B might communicate the replacement condition to a remote communication device. Optionally, a display 114G can be provided for displaying information such as water quality measurements, date of last filter change, and/or remaining filter life (based on known loading specifications of the filter 114B and measurement data obtained by the sensors 114C and 114D).

In still other variations, a third sensor unit 114F configured to be exposed to the fluid that enters the filter housing 114A can be employed, wherein the third sensor 114F is coupled to the processing unit 112A. The processing unit 112A would be in this embodiment configured to operate in conjunction with the first sensor 114C to monitor the fluid, generate a variable based on said monitoring, generate a preliminary identifier if the variable is indicative of a detection condition, and operate in conjunction with the third sensor 114F to determine whether the detection condition has occurred based on new data. As explained above, this monitor and confirm function can be carried out with sensors 111 configured within the same sensor unit 110, but the raw data can be communicated to a central location for this processing, and the central location can then be instructed whether to carry out the confirmation function.

As with other embodiments, this embodiment can include a communication unit 112B configured to report the detection condition to a remote communication device if the processing unit 112A confirms that the detection condition has occurred, and/or provide raw data and/or processed data to a remote communication device. Additionally or alternatively, the processing unit 112 might be configured to generate a sensor alert identifier if the third sensor unit 114F provides a measurement reading that differs by a predetermined amount from a contemporaneous measurement reading of a same type provided by the first sensor unit 114C. This configuration might serve as an indication that the first sensor unit 114C may be faulty. The first sensor unit 114C could then be deactivated by the processing unit 112A.

As with other embodiments disclosed herein the first and second sensor units 114C and 114D can include an ion-selective sensing element capable of measuring an ion content, a chlorine sensing element capable of measuring a chlorine content and a conductivity sensing element capable of measuring electrical conductivity, for example. More generally, the sensors 114C and 114C can comprise at least one of an ion-selective sensing element, an amperometric sensing element, a potentiometric sensing element, a conductivity sensing element, a temperature sensing element, an oxidation-reduction potential sensing element, a chlorine sensing element, an oxygen sensing element, an immunosensor, a DNA probe and an optical sensor.

Figure 1G:
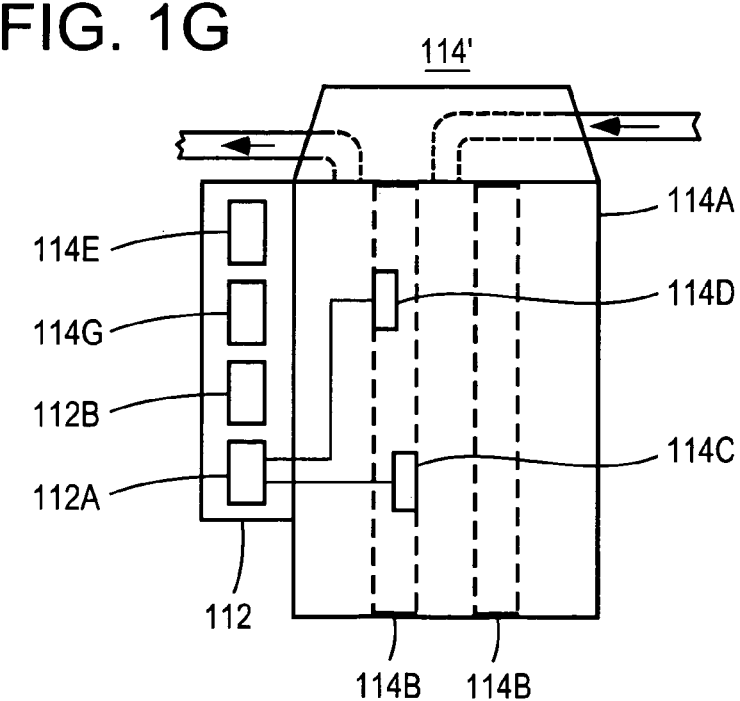
FIG. 1G is an illustration of another exemplary embodiment of a sensor unit.

As also with other embodiments of the present invention, the module 112 can be attached to the filter housing 114A as shown in FIG. 1G, or can be configured as a stand-alone unit coupled to the sensors 114C, 114D via electrical (wired or wireless) connections, wherein the module 112 could be mounted on a wall or plugged into a power outlet. Of course, the processing unit 112A can be in the form of a first processing unit connected to the first sensor unit 114C, and a second processing unit connected to a second sensor unit 114D. The first and second processing units can thereby be configured to compare measurement data generated by the first and second sensor units 114C and 114D.

The processing unit 112A, however physically configured, could be configured to communicate with a communication unit 112B and to instruct the communication unit 112B to report the detection condition to another communication unit if the processing unit 112 confirms that the detection condition has occurred and/or raw data, in this exemplary embodiment.

Although the examples described above have referred to a filter unit 114, the filter unit 114 could be any suitable fluid-treatment device such as, for example, a water-softening device, a distillation device, or a reverse-osmosis or membrane filtration device, media filtration device, or any combination thereof, including or filter housing and/or a filter.

Multiple Sensors with Selective Exposure

Figure 1K:
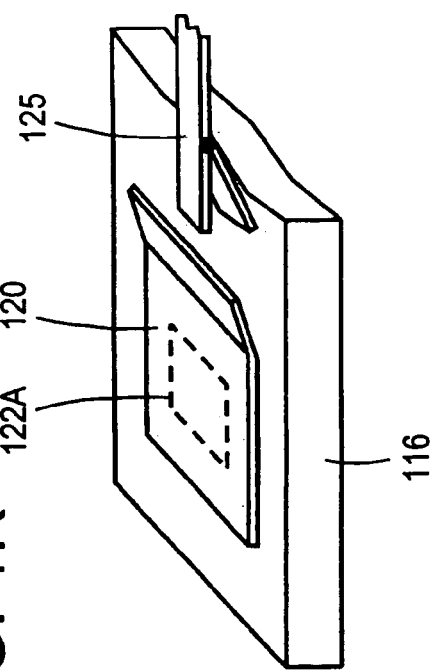
FIG. 1K is an illustration of another exemplary embodiment of a sensor unit.
Figure 1I:
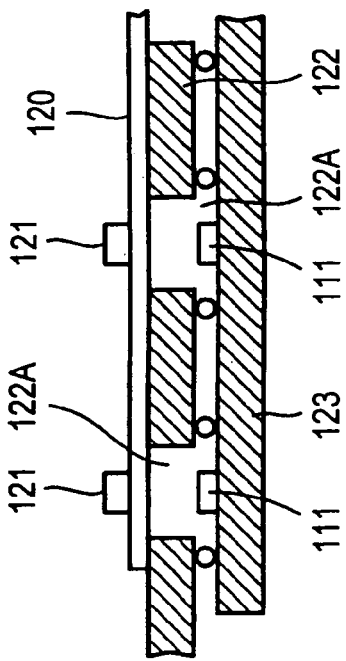
FIG. 1I is an illustration of another exemplary embodiment of a sensor unit.

With reference to FIG. 1D, a multi-sensor apparatus for monitoring a fluid can include a substrate 116 and a plurality of sensors, each of which can include one or more than one sensing element attached to or formed in or on the substrate 116. In FIGS. 1D, 1E and 1I individual sensors are identified by reference numeral 111, and individual sensing elements are identified by reference numeral 113, for brevity. Each sensor 111 is configured to be exposed to a fluid. Also, a mechanism (discussed below) for selectively exposing individual sensors of the plurality of sensors 111 to the fluid is provided in this embodiment. As with other embodiments at least one of the sensors 111 can include a plurality of sensing elements 113 and at least one of the sensors 111 can included both an ion-selective sensing element capable of measuring an ion content and a chlorine sensing element capable of measuring a chlorine content, for instance. More generally, at least one of the sensors 111 can comprise at least one of an ion-selective sensing element, an amperometric sensing element, a potentiometric sensing element, a conductivity sensing element, a temperature sensing element, an oxidation-reduction potential sensing element, a chlorine sensing element, an oxygen sensing element, an immunosensor, a DNA probe and an optical sensor.

As illustrated in FIGS. 1D–1E, the sensors 111 can be formed in recesses 116A. Any mechanism for forming the recesses 116A can be employed, including lithographic patterning and etching processes to produce recesses on the surface the substrate 116. The substrate 16 alternatively can be formed as a first substrate 122 comprising a plurality of apertures 122A extending therethrough, and wherein each sensor 111 is disposed on a surface of a second substrate 123, as shown in FIG. 11. The second substrate 123 is bonded to the first substrate 122 such that each sensor 111 faces a respective aperture 122A, of the first substrate 122, using for example a flip-chip process. Forming the sensors 111 in recesses 116A can be advantageous in embodiments involving mechanisms for selective exposure of multiple sensors 111 as this can protect the surfaces of the sensors 111; however, it is not necessary to form the sensors in recesses in selective exposure embodiments.

As noted above, a mechanism for selectively exposing individual sensors 111 to the fluid can be provided. For example, as illustrated in FIGS. 1D, 1H and 1I, a cover membrane 120 (or multiple cover membranes, one for each sensor 111) can be attached to a surface of a substrate 116, 122, the cover membrane 120 covering the plurality of sensors 111, in the recesses 116A, or below the apertures 122A. A plurality of heating elements 121, for example, can be attached to the membrane 120 at positions proximate to respective sensors 111. Each heating element 121 can be selectively operable to generate an opening in the membrane 120 thereby allowing a particular sensor 111 positioned proximate to a recess 116A or aperture 122A to be exposed to the fluid. As an alternative to using heating elements 121 to selectively expose a sensor 111, any suitable mechanisms which serve to dissolve the membrane or physically remove or tear of at least a portion of the membrane 120 can be used, such as shown in FIG. 1J by a conceptually illustrated mechanical perforator 124 or FIG. 1K by a conceptually illustrated mechanical gripper or scraper 125. The embodiments of FIGS. 1J and 1K illustrate in a generic way any number of mechanical means for selectively removing the membrane 120. In addition, any suitable actuation mechanism(s) can be used enable the mechanical perforator 124 or the mechanical gripper or scraper 125 to be positioned adjacent to a given sensor 111 and to selectively expose that sensor 111. For example, the sensors can be configured along a line or in a two-dimensional array on the substrate 116, and one or more actuators can be used to provide relative linear motion in one or two directions between the substrate 116 and the mechanical member 125, 125. As another example, the sensors 111 can be arranged along the circumference of a circle, and one or more actuators can be used to provide relative rotational motion between the substrate 116 and the mechanical member 124, 125.

As with other embodiments disclosed herein, the substrate 116 can be a silicon substrate or can be another type of substrate such as, for example, ceramic, glass, $SiO_2$, or plastic. An exemplary multi-sensor apparatus can also be fabricated using combinations of such substrates situated proximate to one another. For example, a silicon substrate having some sensor components (e.g., sensing elements) can be mounted on a ceramic, $SiO_2$, glass, plastic or other type of substrate having other sensor components (e.g., other sensing elements and/or one or more reference electrodes). Conventional electronics processing techniques can be used to fabricate and interconnect such composite devices. Each sensor 111 can have one or more corresponding reference electrodes, the reference electrodes being located either on the same substrate as one or more sensors 111 or on or more different substrates. For example, reference electrodes can be fabricated on one or more ceramic, $SiO_2$, glass, or plastic substrates (or other type of substrate), wherein a sealed fluid reservoir is provided in the substrate for a given reference electrode. Alternatively, multiple sensors 111 can share one or more common reference electrodes, the common reference electrode(s) being located on the same substrate as a sensor 111 or on one or more different substrates. Providing separate reference electrodes for each sensor 111 can be beneficial since the performance of reference electrodes can degrade with use. By providing selective exposure of reference electrodes associated with individual sensors 111, sensor performance can be enhanced because fresh reference electrodes can be provided when a new sensor is activated. A reference electrode can be exposed using the same exposure system as a sensor 111 or using a different exposure system.

The membrane 120 can be made of any suitable material such as a polymer material (e.g., polyester or polyimide) for instance and the membrane 120 may be attached to the substrate 116, 122 via an adhesive or may be attached to the substrate 116, 122 by a heated lamination process. The sensors 111 may be lithographically produced (e.g., using known microelectronics processing techniques), dispensed or screen printed, for example, on a recessed or non-recessed surface of the substrate 116.

A multi-sensor apparatus can enable carrying out a confirmation function as discussed above by allowing the processing unit 112A to selectively expose a desired sensor in response to a measurement by another sensor indicative of a detection condition. The processing unit 112A can trigger a power circuit to direct power to a heater 121 to expose the desired sensor 111.

Figure 1L:
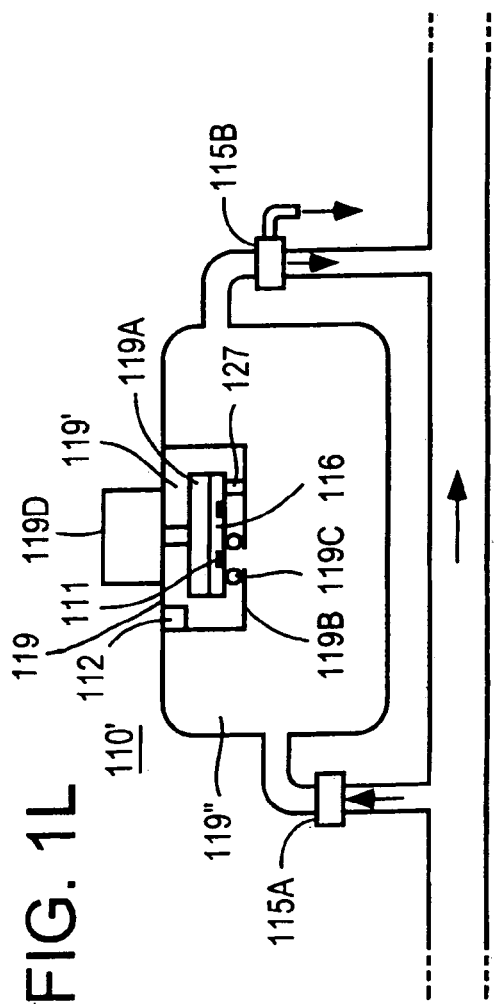
FIG. 1L is an illustration of another exemplary embodiment of a sensor unit.

Another exemplary embodiment for selectively exposing sensors 111 is illustrated in FIG. 1L. As shown in FIG. 1L, a sensor unit 110' is connected to a fluid source via an input valve 115A and an output valve 115B. The sensor unit 110' comprises a housing member 119 with a wall 119B to provide a sensor cavity 119' and a fluid cavity 119". A substrate 116 is provided on a backing plate 119A in the sensor cavity 119' adjacent to an aperture in the wall 119B to allow a sensor 111 to be exposed to a fluid. A seal 119C, such as an o-ring, arranged adjacent to the aperture and positioned between a surface of the substrate 116 and a surface of the wall 119B of the housing member 119, to seal the substrate 116 against the housing wall 119B. An actuator 119D moves the backing plate 119A and the substrate 116 to selectively locate an individual sensor 111 to a region of the aperture such that the particular sensor 111 is exposed to the fluid. The substrate 116 is preferably flat to allow for a good seal, but the invention is not so limited. As discussed previously, sensors 111 can be formed on a recessed or non-recessed surface of the substrate 116. To minimize the potential for fluid leakage into the sensor cavity 119', the valves 115A and 115B can be actuated to partially or substantially drain the fluid cavity 119" before selectively exposing a new sensor 111 with the actuator 119D.

Figure 1M:
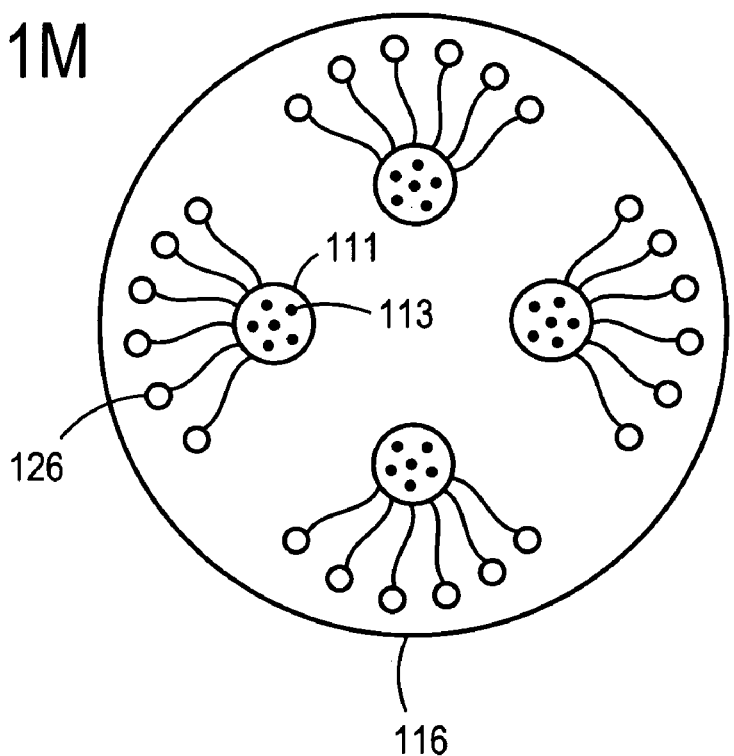
FIG. 1M is an illustration of another exemplary embodiment of a sensor unit.
Figure 1N:
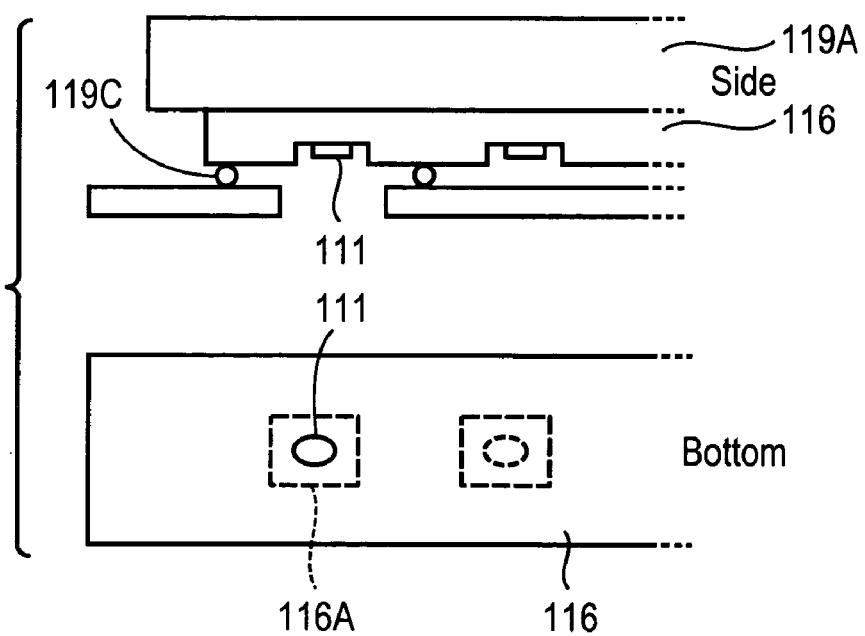
FIG. 1N is an illustration of another exemplary embodiment of a sensor unit.

The sensors 111 can be lithographically produced, deposited or screen printed on a recessed or non-recessed surface of the substrate 116, and might be formed at the circumference of a circle so as to allow the actuator 119D to be a simple carousel mechanism using rotational motion as shown in FIG. 1M, or can be formed in a staggered or straight line as shown in FIG. 1N, or in a two-dimensional array, for instance, and the actuator 119D can provide for a linear motion in one or more dimensions. The substrate can be in the form of substrate 116 with recesses 116A as shown in FIGS. 1N and 1E, or can be in the form of the flip-chip bonded substrate 122, 123 shown in FIG. 1F.

In view of the above, it will be apparent that carousel or linear motion embodiments can be used in conjunction with sensors 111 covered by at least one membrane 120 attached to a surface of the substrate 116 (e.g., FIGS. 1J and 1K), in which case a mechanical member 124, 125 selectively displaces or perforates the at least one membrane 120 in a region proximate to an individual sensor 111 to allow the particular sensor 111 to be exposed to a fluid. In this regard, a configuration similar to that illustrated in FIGS. 1L and 1M (or 1N) can be used. The actuator 119D can provide relative motion between the substrate 116 (mounted on backing plate 119A) and the mechanical member 124, 125 to allow the mechanical member 124, 125 to selectively displace the at least one membrane 120. The seal 119C and housing 119 may not be necessary in embodiments involving a membrane 120.

In the embodiments in which motion of the sensors 111 is designed to occur, electrical connections 126 could be configured to align with a contact pad 127 or pads to assure electrical connection between the sensors components 111, 113 and the processor 112A.

Distribution of Sensor Elements

Figure 2:
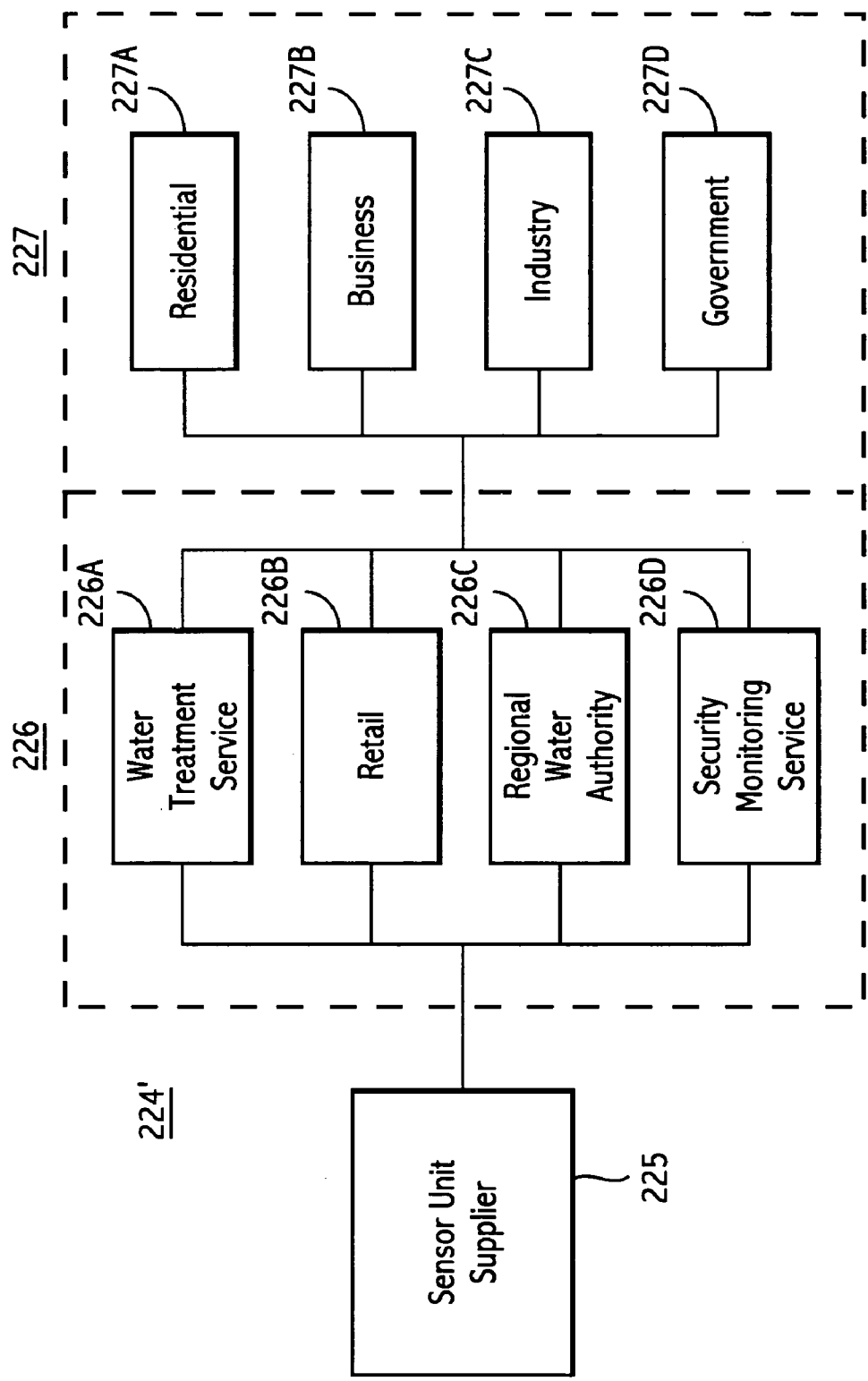
FIG. 2 is a block diagram of an exemplary sensor unit supply chain in accordance with aspects of the present disclosure.

Unlike some prior systems which required the regional water authority to install water quality measuring devices at various points within the water treatment plants and/or within a water distribution network, the present inventors have devised a mechanism wherein the distribution of sensor units can utilize pre-existing commercial distribution systems 224, such as illustrated in the exemplary embodiment shown in FIG. 2. For instance, a sensor unit supplier 225 (e.g., an original equipment manufacturer, reseller or wholesaler) can supply or arrange to have supplied sensor units 110 to pre-existing product distributors 226, which might include among others water treatment services 226A, such as Culligan Water Treatment Services, Ecco Water Systems, Mlllipore Corporation, and GE Specialty Materials, for example. These water treatment services 226A provide equipment and/or consumable supplies for treating water such as softening agents, filtration devices, filters, etc. to residential locations (e.g., houses, apartments, mobile homes, etc.) 227A, businesses 227B, industrial plants 227C and/or government facilities 227D. The water treatment services 226A provide sales, distribution and installation of the sensor units 110 through preexisting commercial distribution systems 224, thereby minimizing the cost of establishing supply chains of sensor units 110 to end users 227 at residential locations 227A, businesses 227B, industrial plants 227C and government facilities 227D, for example, or any location that would want or use the services of a water treatment service 226A, for example. Alternatively or additionally, the government regional water authority can be utilized as an installer of sensor units at the water authority's existing sensor locations and/or additional locations, and/or can also be utilized as a distributor of sensor units to homes, businesses, industrial plants, and government facilities, wherein monitoring of the sensor units can be carried out by another entity other than the regional water authority.

For instance, water treatment services 226A can receive sensor units 110 from a sensor unit supplier 225 for installation at the sites of the end users 227. The water treatment service 226A can sell the sensor units 110 as an added value to their overall water treatment service, as explained in more detail with reference to FIG. 3, below. Water treatment services 226A thereby act as sales and distribution networks for the installation of sensor units 110 at the end users 227. Additionally, because water treatment services 226A often install the equipment they are selling, leasing or otherwise conveying to the end user 227, this installation can include installation of the sensor units 110, and can further include establishing communication between the sensor units 110 and centralized data collection points such as the water treatment service 226A, smart nodes 332 and/or a single centralized data collection point 333 within a water monitoring network of a geographic or political region or regions, as explained with reference to FIG. 3, below. The water treatment service 226A can thus carry out on-line monitoring of intake water and treated (e.g., filtered) water and, as mentioned previously, can also utilize such monitoring to guarantee or certify the quality of treated water at end-user delivery points 227A–227D.

Alternatively, the sensor unit supplier 225 can supply sensor units 110 or cause them to be supplied directly to the retail outlets 226B (e.g., retail outlets in physical buildings or retail outlets provided through Internet websites, or both) or through wholesale outlets to retail outlets 226B. The end users 227 would then obtain sensor units 110 directly from retail outlets 226B for self-installation or end-user assisted installation. Hence, the retail outlet 226B provides the sales and distribution mechanism, whereas the end user 227 provides installation of the sensor units 110 at points of end use of the water in the water distribution system. The end user 227 would then establish or facilitate establishment of communication with a monitoring network 330. In some instances, the sensor unit 110 can include a cellular communication device with its own unique identification code. The end user 227 can simply turn on the cellular communication device and either enter the end user's location or address, or allow the cellular communication device to be located through triangulation if that capability exists within a particular cellular system. Of course, this mechanism could be employed regardless of how the sensor unit 110 was distributed.

Another form of preexisting commercial distribution system 224 includes regional water authorities 226C which, in the regular course of their activities, installs water meters and the like at the locations of end users 227, whether residential 227A, businesses 227B, industrial plants 227C or government facilities 227D. The sensor units 110 would simply be installed by the regional or multi-regional water authority 226C or its contractors. In this circumstance, there may not be an actual sale or other conveyance of the sensor unit 110 to the end user, who may not even be aware of the installation. Meter manufacturers can incorporate sensor unit capabilities into standard meters for selective activation by the regional water authority 226C, by the meter manufactures or another entity interested in providing data from end-point locations within a water distribution system. Here it can be seen that the invention can be used in conjunction with other fluids, such as natural gas, if there is a need or a need develops.

Additionally or alternatively, home security, home (e.g., utility) monitoring, and health monitoring services 226D can provide sales, distribution and installation of sensor units 110 as part of or as value added to the offered monitoring services. For instance, home security and health monitoring services 226D, as well as generalized home monitoring services which may include monitoring the usage of utilities, can add water quality monitoring capabilities as part of their services. The sales, distribution and installation of sensor units 110 would then use the same network these services have established to sell, distribute and install other equipment to perform other home and health monitoring functions.

As should be appreciated by the above, the sensor unit distribution system 224 for distributing sensor elements 110 utilizes one or more pre-existing commercial distribution systems 226 to sell, distribute and install sensor units 110 at the location of the end user 227. Virtually any product distribution system reaching residences 227A, businesses 227B, industrial plants 227C and/or government facilities 227D (or any locations where water is used by end users in a water distribution system) can be used to also distribute sensor units 110, perhaps as added value services or products. The thus distributed sensor units 110 can form a water monitoring network 330 specific to the particular pre-existing product distribution system 226, or sensor units 110 distributed by a variety of pre-existing product distribution systems 226 form a larger water monitoring network 330, or a mixture wherein certain data gathered by sensor units 110 distributed by a particular pre-existing product distribution system 226 would be proprietary to the particular pre-existing product or service distributor 226 (e.g., data related to water treatment equipment performance), but other data (e.g., data related to water quality within a water distribution system) would be provided to a water quality monitoring network 330. In this way, a larger and perhaps more distributed panel of sensor units 110 can be distributed and installed at relatively little cost to the water authorities, for instance.

With reference to FIG. 3, various aspects of the present disclosure including data collection, centralized or distributed data analysis and data distribution will be explained by way of an exemplary water monitoring system 330. In the exemplary water monitoring system 330, various sensor units 110A–110F at sites A–F are connected to the water quality monitoring system 330 by communication links as identified above with reference to the details of the sensor units 110. While six sensor units 110A-110F are shown in FIG. 3, many more are contemplated and the drawings should not be relied upon for judging orders of magnitude or the number of sensor units 110, smart nodes 332 or centralized data collection points 333.

The sensor units 110A–110C, for instance, are connected to a smart node 332A (a node that has data processing power), whereas other sensor units 110D–110F may be connected to a separate smart node 332B or the same smart node 332A as warranted by various factors involving the network and water authorities, including the bandwidth of communication devices, the appropriateness of distributing processing an analysis of data, etc. The smart nodes 332 can have a relationship to the region or authority of regional water authorities 226C, for example.

The sensor units 110 may provide raw data, or just confirmed detection events to smart nodes 332 and/or directly to a centralized data collection point 333. The double-sided arrow lines in FIG. 3 indicate the flow of data up the hierarchical network 330, and data and inquiries down the hierarchical network 330, there being contemplated two-way communication in some embodiments. In certain embodiments, only communication going up the hierarchical chain is necessary.

The smart nodes 332 may process the raw data to monitor, identify and confirm detectable events in the water quality. Alternatively, the sensor units 110 can provide monitoring, identifying, confirming and reporting functions to the smart nodes 332 or centralized data collection points 333. Whether the smart nodes 332 process raw data or rely upon the sensor units 110 for confirmed data, the smart nodes 332 having received data from a variety of sensor units 110A–10F at a variety of sites 110A–110F can aggregate and further process such data to determine historical water quality measures, overall quality measures, trends and multipoint measures of a regional water distribution pipe system. The introduction point or source of possible contaminants, water main breaks, freezing pipes, etc., can be traced by analysis of the multipoint data gathered at smart nodes 332 or centralized data collection points 333 by mapping techniques based on the locations of the sensor units 110 within a water distribution system and the measure and/or reported events from the distributed sensor units 110.

The data collection can run in real time, and can continuously, or intermittently (e.g., periodically at pre-set time intervals) monitor fluid quality, or upon inquiry, or operate based on stored data at the sensor sites 110A–110F, depending on the data storage and communication capabilities of the sensor units 110. Real-time data has obvious advantages and it should be noted that most types of sensor units 110 contemplated above measure in real time (whether continuously, periodically or upon inquiry), rather that taking samples and testing the samples at a later time.

Additionally, the smart nodes 332 may periodically or at the command of an operator inquire as to measured data from the sensor units 110 as communication protocols or information needs might dictate. The centralized data collection as represented by the smart nodes 332 and the centralized data collection point 333 can be conducted over private or public networks (e.g., VPN, WAN, the World Wide Web including the Internet), dedicated telephone lines, cellular networks, or virtually any other form of communication. For instance, telephone land-lines and telephone wireless networks can be utilized for a call-up by the sensor units 110 for periodic interrogation by the smart nodes 332 or centralized data collection point 333 of the sensor units 110. Additionally, other communication protocols can be used including communications over a pre-existing power grid by a super-imposed carrier over a power line using known or future protocols and techniques. Further, acoustic waves carried by water in the water distribution system can be utilized for information transmissions. Other communication mechanisms can be utilized independently or in combination, including fiber optics, satellite communications and virtually any communication protocol or mechanism capable of transmitting raw and/or analyzed data between the sensor units 110 and the smart nodes 332 and/or centralized data collection points 333.

Additionally and/or alternatively, the sensor units 110D–10F can communicate to smart nodes 332 and/or centralized data collection points 333 through other entities such as water treatment services 226A, home monitoring (security and utility) services and/or health monitoring services 226D, retail outlets 226B, and/or regional water authorities 226C, which would then convey data to smart nodes 332B, as illustrated in the exemplary embodiment shown in FIG. 3.

With respect to data distribution, once the data has been gathered and analyzed, raw data, analyzed data and aggregated data can be distributed, whether from smart nodes 332 that may be regional and/or that may be specific to regional water authorities, or to centralized data collection points 333 that may be multi-regional in nature. The types of data can be categorized as data containing user identifiable information and aggregated data, which may or may not contain user identifiable information.

Data containing user identifiable information is useful for end users 227 for a variety of reasons. For instance, for sensor units 110 that include a sensor 111 or sensor element(s) 113 or sensor groups positioned after a water treatment device such as a water softener or filter 114, data relating to a parameter indicating a water quality detection event can be utilized by the end user 227 to inform him or her that filters and/or water treatment chemicals need to be replaced or replenished as the situation dictates. This can be done at the sensor unit 110 by indicators or the like, or through communications from smart nodes 332 or centralized data collection points 333. The end user 227 may also be interested in the performance of the local regional water authority 333C to serve as a check upon the performance of the regional water authority 226C insofar as the end user 227 may question the regional water authority 226C when the water quality has been reduced or changed.

Raw and analyzed data from the smart nodes 332 can be provided to regional water authorities 226C for determining compliance with water quality standards and as internal checks on the performance of the regional water authority 226C. Additionally, raw and analyzed data from smart nodes 332 and/or centralized data collection points 333 can be supplied to multi-regional water authorities 335 such as national water authorities to determine compliance with appropriate water quality standards by regional water authorities 226C and as determinations of the overall health of the multi-regional water supply to detect the presence, persistence and extent of contaminants in the multi-regional water supply so as to determine or trace the origin and extent of problems within the water supply. Additionally, the information can be supplied back to preexisting commercial distribution systems 224.

For instance, water treatment services 226A might be interested in determining the water quality of water leaving water treatment devices installed at the location of end users 227 and may be interested in the water quality of the water entering the water treatment devices, so as to alert end users 227 of the need for replenishing chemical supplies and/or replacing filters, or automatically providing the end user 227 with such supplies, or to alert the end user 227 of problems with the water supply, particularly those not correctable by the water treatment devices, as the terms of any agreement between the water treatment service 226A and the end user 227 may dictate. Such alerts can be provided in a variety of ways, such as, using local indicator (e.g., a light, audible alarm, or other form of alert on the sensor unit housing), displaying information on a display (e.g., a display located on the sensor unit housing), making a telephone call to the end user, or sending an electronic message (e.g., e-mail, pager message, SMS, etc.) to the end user, or any combination of these approaches. Moreover, if potentially dangerous water quality conditions are detected, an alert can also be sent to the regional water authority. For example, if an identification event (e.g., relating to a potentially dangerous condition) is detected through comparison of sensor data with a database of potential chemical profiles, a corresponding alert can be sent to both the end user and the regional water authority. Also, depending upon the condition identified, a suitable control valve(s) can be operated to shut off the water supply to the end user as discussed previously.

Further, where water treatment devices (e.g., filters) are distributed to be associated with sensor units, water treatment services can guarantee or certify the quality of water treated by the water treatment devices as an additional service to end users. Moreover, customers can be billed per unit of water treated by the water treatment devices, either in place or, or in addition to, being billed for the water treatment devices and/or consumables themselves.

With respect to retail outlets 226B, the retail outlet 226B can use the data to prompt end users 227 to purchase additional filters and/or chemicals and/or replace filtration and treatment devices based on a measure of the water quality either entering and/or exiting such devices.

The raw and analyzed data can also be provided to home monitoring and health monitoring services 226D for the benefit of informing the end users 227 as to the quality of the water entering the domain of the end user 227.

In addition to the foregoing entities 226A–226D, 335 that might be interested in the quality of water at the location of the end user 227, other entities may be interested in the quality of water reaching end users 110. For instance, water quality watch groups may be interested in aggregated data to determine trends in the water quality to rate and impose pressure on regional and multi-regional water authorities 226C, 335. Government entities may be interested in determining the viability of the water distribution infrastructure both on a regional and multi-regional scale. Academics may be interested in the data to determine global trends in water quality. Real estate sales facilitators may be interested in identifying water quality as one factor among many factors that might be used in a home owner's decision to buy or sell an individual house within a particular region. Government agencies such as the U.S. Center for Disease Control, Evironmental Protection Agency, Department of Homeland Security, and hospitals may be interested in the data to alert the public and/or determine the origin and spread of disease, toxins or other issues of health having origins in the water supply that might concern a community or a nation. Aggregated data can be used to determine trends, and/or user identifiable data may be used to pinpoint particular sources of problems in regional water distribution networks or multi-regional water distribution networks. The underlying theme is that the water monitoring system provides a mechanism wherein various types of information concerning water quality can be shared and/or sold to a variety of interested parties on exclusive or non-exclusive bases by a party that can be relatively neutral and independent.

Consideration for End Users and for Access to Data

Insofar as end users 227 are asked to install or permit the installation of sensor units 110 capable of communicating data outside the domain of the end users 227, some consideration to the end user 227 would seem appropriate in some circumstances. For instance, the end user 227 may view as consideration the ability of the sensor unit 110 and/or water quality monitoring system 330 of which his or her sensor unit 110 is part to alert him of potential hazards that may not otherwise be available. For instance, to obtain the function of having a local indicator provide information about water quality, the end user 227 might have to agree to share information with a water quality monitoring system 330. Alternatively or additionally, the end user 227 might agree to obtain the benefit of analysis that are not detectable via the processing power of a individual sensor unit 110 at a price point the end user 227 is willing to pay. Hence, the consideration for the communication of data to a water quality monitoring system 330 would be the value added to sensor units 110 a price point that the end user 227 is willing to pay.

Additionally, the end user 227 would likely be aware or be made aware that the communicated information is to the benefit of the overall community. It would appear that the end user 227 would have a small threshold in the way of privacy concerns insofar as the volume of water use is already monitored at the end user location and the end user 227 imparts no private or personal information upon the quality of the water and therefore the information developed by the sensor units 110.

Additionally or alternatively, the sale or other conveyance of the sensor unit 110 can be conditioned upon the agreement by the end user 227 for the transmission of data to smart nodes 332 or centralized data collection points 333. Further, sale of the equipment, subscription of monitoring or water treatment services 226A and other subscription based services can provide consideration to the end user 110 as well as lend/lease, can be condition upon providing the communication link and the data provided by the sensor units 110.

Additionally, water authorities 226C can require the installation of sensor units 110 as part of services such as the supply of water or other services generally provided by local governments. Finally, the sensor units 110 may be required to be installed by the end user 227 or be permitted by the end user 227 to be installed by regulation of government.

As consideration for access to both raw and analyzed data, those wishing to access the data can do so by subscription base payments either of a periodic nature (e.g., monthly and/or yearly payments), fully paid-up licenses, fees or per individual reports or a combination thereof. Additionally, fees could be based upon the report of any particular detected event or based on the number of detected events per report. Aggregated data reports can add value by providing historical data, comparison data or other added value imparted by the intelligence and data bases of the reporter service or entity, such that the raw data, the individually end user identifiable data, and the aggregated data can be analyzed by informed individuals and/or through algorithms to provide enhanced value to the quality of the data being reported. Compensation can take the form of payments by entities capable of assisting the end user 227 as part of consideration for any such referral or identification of prospective end users 110 in need of assistance.

As can be seen, the present disclosure has been explained by way of exemplary embodiments which it is not limited. Various modifications and alterations of the core concepts will occur to those skilled in the art without departing from the scope of the invention as articulated in the claims appended hereto. It is reiterated that advantages and attendant aspects of various embodiments of the invention are not necessarily part of the invention. Rather, the invention should be determined by a review of the claims appended hereto, as well as equivalents of the elements thereof.

What is claimed is:

1. A system for monitoring potable water, comprising:
a fluid treatment device configured for treating potable water;
a first sensor configured to be exposed to pre-treatment potable water that enters the fluid treatment device, the first sensor comprising a plurality of sensing elements that are disposed on a substrate, said first sensor being configured to measure multiple different chemical species; and
a second sensor configured to be exposed to post-treatment potable water.

2. The system of claim 1, wherein the fluid treatment device comprises at least one of a filter housing, a filter, a water-softening device, a distillation device, and a reverse-osmosis filtration device.

3. The system of claim 1, wherein the fluid treatment device comprises a filter housing for holding a filter, the first sensor being configured to be exposed to pre-treatment potable water and the second sensor being configured to be exposed post-treatment potable water.

4. The system of claim 1, wherein the second sensor comprises a plurality of sensing elements.

5. The system of claim 1, wherein the first sensor comprises at least one of an ion-selective sensing element, an amperometric sensing element, a potentiometric sensing element, a conductivity sensing element, a temperature sensing element, an oxidation-reduction potential sensing element, a chlorine sensing element, an oxygen sensing element, an immunosensor, a DNA probe and an optical sensor.

6. The system of claim 5, wherein the second sensor comprises at least one of an ion-selective sensing element, an amperometric sensing element, a potentiometric sensing element, a conductivity sensing element, a temperature sensing element, an oxidation-reduction potential sensing element, a chlorine sensing element, an oxygen sensing element, an immunosensor, a DNA probe and an optical sensor.

7. The system of claim 1, further comprising a processing unit coupled to the first and second sensors, the processing unit being configured to compare measurement data generated by the first and second sensors.

8. The system of claim 7, further comprising a communication unit coupled to the processing unit, the communication unit being configured to communicate measurement results generated by the processing unit to a remote communication device.

9. The system of claim 7, wherein the processing unit comprises a first processing unit and a second processing unit, wherein the first processing unit is arranged with and coupled to the first sensor, and wherein the second processing unit is arranged with and coupled to the second sensor.

10. The system of claim 3, wherein the first and second sensors are attached to the filter housing.

11. The system of claim 3, further comprising a filter that filters the potable water.

12. The system of claims 11, wherein the first and second sensors are attached to the filter.

13. The system of claim 11, wherein the first and second sensors are embedded within the filter.

14. The system of claim 7, wherein the processing unit is configured to generate an identifier to indicate a replacement condition for a filter to be placed in the filter housing based upon the comparison of the measurement data from the first and second sensors.

15. The system of claim 14, further comprising an indicator that indicates the replacement condition for the filter.

16. The system of claim 14, further comprising a communication unit that communicates the replacement condition to a remote communication device.

17. The system of claim 7, further comprising a third sensor configured to be exposed to the pre-treatment potable water,
wherein the third sensor is coupled to the processing unit, and
wherein the processing unit is configured to
operate in conjunction with the first sensor to monitor the pre-treatment potable water,
generate a variable based on said monitoring,
generate a preliminary identifier if the variable is indicative of a detection condition, and
operate in conjunction with the third sensor to determine whether the detection condition has occurred based on new data.

18. The system of claim 17, further comprising a communication unit configured to report the detection condition to a remote communication device if the processing unit confirms that the detection condition has occurred.

19. The system of claim 7, further comprising a third sensor configured to be exposed to the pre-treatment potable water,
wherein the third sensor is coupled to the processing unit, and
wherein the processing unit is configured to generate a sensor alert identifier if the third sensor provides a measurement reading that differs by a predetermined amount from a contemporaneous measurement reading of a same type provided by the first sensor.

20. The system of claim 19, wherein the sensor alert identifier is indicative that the first sensor may be faulty.

21. The system of claim 1, wherein at least one of the first and second sensors is recalibrated by another sensor sensing substantially the same fluid conditions of the potable water.

22. The system of claim 7, wherein the processing unit is configured to provide raw data generated by first and second sensors to the communication unit for communicating the raw data to a remote communication device.

23. The system of claim 8, wherein the processing unit is configured to provide processed data, locally processed by the processing unit, to the communication unit for communicating the processed data to the remote communication device.

24. The system of claim 8, wherein the processing unit is configured to receive an instruction from the remote communication device via the communication unit instructing the processing unit to determine in conjunction with the second sensor whether the detection condition occurred.

25. The system of claim 1, wherein the fluid treatment device comprises a filter,
wherein the first sensor is attached to the filter, the first sensor being configured to be exposed to pre-treatment potable water, and
wherein the second sensor is attached to the filter, the second sensor being configured to be exposed to post-treatment potable water.

26. The system of claim 25, wherein the second sensor comprises a plurality of sensing elements.

27. The system of claim 25, wherein the first sensor comprises an at least one of an ion-selective sensing element, an amperometric sensing element, a potentiometric sensing element, a conductivity sensing element, a temperature sensing element, an oxidation-reduction potential sensing element, a chlorine sensing element, an oxygen sensing element, an immunosensor, a DNA probe and an optical sensor.

28. The system of claim 27, wherein the second sensor comprises an at least one of an ion-selective sensing element, an amperometric sensing element, a potentiometric sensing element, a conductivity sensing element, a temperature sensing element, an oxidation-reduction potential sensing element, a chlorine sensing element, an oxygen sensing element, an immunosensor, a DNA probe and an optical sensor.

29. The system of claim 25, further comprising a processing unit attached to the filter, the processing unit being configured to compare measurement data generated by the first and second sensors.

30. The system of claim 25, further comprising an interface attached to the filter that allows the first and second sensors to communicate with a processing unit located outside the filter.

31. The system of claim 25, further comprising:
a first processing unit arranged with and coupled to the first sensor; and
a second processing unit arranged with and coupled to the second sensor, the first and second processing units being configured to compare measurement data generated by the first and second sensors.

32. The system of claim 25, wherein the first and second sensors are embedded within the filter.

33. The system of claim 29, wherein the processing unit is configured to generate an identifier to indicate a replacement condition for the filter based upon the comparison of the measurement data from the first and second sensors.

34. The system of claim 31, wherein the first and second processing units are configured to generate an identifier to indicate a replacement condition for the filter based upon the comparison of the measurement data from the first and second sensors.

35. The system of claim 25, further comprising a third sensor attached to the filter.

36. The system of claim 35, wherein the third sensor comprises a plurality of sensing elements configured to be exposed to pre-treatment potable water.

37. The system of claim 29, further comprising a third sensor attached to the filter and having a plurality of sensors configured to be exposed to pre-treatment potable water, wherein the third sensor is coupled to the processing unit,
wherein the processing unit is configured to
operate in conjunction with the first sensor to monitor the pre-treatment potable water,
generate a variable based on said monitoring,
generate a preliminary identifier if the variable is indicative of a detection condition, and operate in conjunction with the third sensor to determine whether the detection condition has occurred based on new data.

38. The system of claim 37, wherein the processing unit is configured to communicate with a communication unit and to instruct the communication unit to report the detection condition to another communication unit if the processing unit confirms that the detection condition has occurred.

39. The system of claim 29, further comprising a third sensor attached to the filter and having a plurality of sensing elements configured to be exposed to pre-treatment potable water, wherein the third sensor is coupled to the processing unit, and wherein the processing unit is configured to generate a sensor alert identifier to be communicated to an indicator if the third sensor provides a measurement reading that differs by a predetermined amount from a contemporaneous measurement reading of a same type provided by the first sensor.

40. The system of claim 39, wherein the sensor alert identifier is indicative that the first sensor may be faulty.

41. The system of claim 29, wherein the processing unit is configured to provide raw data generated by first and second sensors to the communication unit for communicating the raw data to the remote communication device.

42. The system of claim 29, wherein the processing unit is configured to provide processed data, locally processed by the processing unit, to the communication unit for communicating the processed data to a remote communication device.

43. The system of claim 29, wherein the processing unit is configured to receive an instruction from a remote communication device via the interface instructing the processing unit to determine in conjunction with the second sensor whether the detection condition occurred.

44. A method for monitoring potable water, comprising:
sensing pre-treatment potable water that enters a fluid treatment device with a first sensor configured to be exposed to the pre-treatment potable water, the first sensor comprising a plurality of sensing elements that are disposed on a substrate, said first sensor being configured to measure multiple different chemical species; and
sensing post-treatment potable water treated by the fluid treatment device with a second sensor configured to be exposed to the post-treatment potable water.

45. The system of claim 1, wherein the second sensor comprises multiple sensing elements that are disposed on a substrate, said second sensor being configured to measure multiple different chemical species.

46. The method of claim 44, wherein the second sensor comprises multiple sensing elements that are disposed on a substrate, said second sensor being configured to measure multiple different chemical species.

47. The method of claim 44, further comprising:
sensing the pre-treatment potable water with a third sensor configured to be exposed to the pre-treatment potable water; and processing measurement data from said first, second and third sensors with a processing unit,
wherein the processing unit is configured to
generate a variable based on measurement data from the first sensor,
generate a preliminary identifier if the variable is indicative of a detection condition, and
determine whether the detection condition has occurred based on comparing measurement data from the third sensor with measurement data from the first sensor.

48. The method of claim 44, further comprising:
sensing the pre-treatment potable water with a third sensor configured to be exposed to the pre-treatment potable water; and
processing measurement data from said first, second and third sensors with a processing unit,
wherein the processing unit is configured to generate an alert identifier if the third sensor provides a measurement reading that differs by a predetermined amount from a contemporaneous measurement reading of a same type provided by the first sensor.

49. The method of claim 47, wherein the third sensor comprises multiple sensing elements that are disposed on a substrate, said third sensor being configured to measure multiple different chemical species.

50. The method of claim 48, wherein the third sensor comprises multiple sensing elements that are disposed on a substrate, said third sensor being configured to measure multiple different chemical species.

51. The method of claim 44, further comprising, further comprising:
processing measurement data from said first and second sensors with a processing unit coupled to the first and second sensors; and
communicating, via a communication device coupled to the processing unit, measurement results generated by the processing unit to a remote communication device.

52. The method of claim 44, further comprising recalibrating at least one of the first and second sensors by another sensor sensing substantially the same fluid conditions of the potable water.

53. The system of claim 1, wherein the fluid treatment device, the first sensor and the second sensor are configured as a unit.

54. The method of claim 44, wherein the fluid treatment device, the first sensor and the second sensor are configured as a unit.

55. The method of claim 44, comprising:
filtering the potable water with a filter arranged with the fluid treatment device; and
generating an identifier to indicate a replacement condition for the filter based upon a comparison of measurement data from the first and second sensors.

* * * * *